United States Patent
Kennedy et al.

(10) Patent No.: US 12,252,710 B2
(45) Date of Patent: Mar. 18, 2025

(54) CATIONIC DENDRIMERS FOR THE CULTURE OF ADHERENT CELLS

(71) Applicant: THE ROYAL INSTITUTION FOR THE ADVANCEMENT OF LEARNING/MCGILL UNIVERSITY, Montréal (CA)

(72) Inventors: Timothy E. Kennedy, Montreal (CA); Jean-Pierre Clement, Montreal (CA); Laila Al-Alwan, Montreal (CA)

(73) Assignee: THE ROYAL INSTITUTION FOR THE ADVANCEMENT OF LEARNING/MCGILL UNIVERSITY, Montréal (CA)

( * ) Notice: Subject to any disclaimer, the term of this patent is extended or adjusted under 35 U.S.C. 154(b) by 0 days.

(21) Appl. No.: 17/724,038

(22) Filed: Apr. 19, 2022

(65) Prior Publication Data
US 2023/0016634 A1    Jan. 19, 2023

Related U.S. Application Data

(60) Provisional application No. 63/219,083, filed on Jul. 7, 2021.

(51) Int. Cl.
*C12N 5/0793*    (2010.01)
*C12M 1/12*    (2006.01)
*C12N 5/079*    (2010.01)

(52) U.S. Cl.
CPC ........... *C12N 5/0619* (2013.01); *C12M 25/04* (2013.01); *C12N 5/0622* (2013.01); *C12N 2500/32* (2013.01); *C12N 2500/38* (2013.01); *C12N 2501/11* (2013.01); *C12N 2501/115* (2013.01); *C12N 2501/119* (2013.01); *C12N 2501/13* (2013.01); *C12N 2506/45* (2013.01); *C12N 2533/40* (2013.01); *C12N 2533/52* (2013.01); *C12N 2535/10* (2013.01)

(58) Field of Classification Search
CPC ................ C12N 5/0619; C12N 5/0622; C12N 2500/32; C12N 2500/38; C12N 2501/11; C12N 2501/115; C12N 2501/119; C12N 2501/13; C12N 2506/45; C12N 2533/40; C12N 2533/52; C12N 2535/10; C12M 25/04; C12M 21/08; C12M 23/20; C12M 25/06
See application file for complete search history.

(56) References Cited

FOREIGN PATENT DOCUMENTS

| WO | WO 2003/033027 A2 | 4/2003 | |
|---|---|---|---|
| WO | WO 2016/166317 A1 | 10/2016 | |
| WO | WO-2019104154 A1 * | 5/2019 | ............ C12M 25/16 |

OTHER PUBLICATIONS

Staehlkea et al., Terminal chemical functions of polyamidoamine dendrimer surfaces and its impact on bone cell growth; Materials Science & Engineering C 101 (2019) 190-203 (Year: 2019).*
Calderon et al., Dendritic Polyglycerols for Biomedical Applications, Adv. Mater. 2010, 22, 190-218 (Year: 2010).*
Kleinman, H.K., Luckenbill-Edds, L., Cannon, F.W. and Sephel, G.C., 1987. Use of extracellular matrix components for cell culture. Analytical biochemistry, 166(1), pp. 1-13. (Year: 1987).*
Haastert, Kirsten, et al. "Establishment of cocultures of osteoblasts, Schwann cells, and neurons towards a tissue-engineered approach for orofacial reconstruction." Cell Transplantation 15.8-9 (2006): 733-744. (Year: 2006).*
Kleinman, H.K., McGarvey, M.L., Hassell, J.R., Star, V.L., Cannon, F.B., Laurie, G.W. and Martin, G.R., 1986. Basement membrane complexes with biological activity. Biochemistry, 25(2), pp. 312-318. (Year: 1986).*
Kawase, Masaya, et al. "Effectiveness of polyamidoamine dendrimers modified with tripeptide growth factor, glycyl-l-histidyl-l-lysine, for enhancement of function of hepatoma cells." Journal of bioscience and bioengineering 88.4 (1999): 433-437. (Year: 1999).*
Lerman, Max J., et al. "The evolution of polystyrene as a cell culture material." Tissue Engineering Part B: Reviews 24.5 (2018): 359-372. (Year: 2018).*
Fernandes, E.G.R., Queiroz, A.A.A.D., Abraham, G.A. and Román, J.S., 2006. Antithrombogenic properties of bioconjugate streptokinase-polyglycerol dendrimers. Journal of Materials Science: Materials in Medicine, 17, pp. 105-111. (Year: 2006).*
Khandare, J., Mohr, A., Calderon, M., Welker, P., Licha, K. and Haag, R., 2010. Structure-biocompatibility relationship of dendritic polyglycerol derivatives. Biomaterials, 31(15), pp. 4268-4277. (Year: 2010).*
Banker, G. A.: 1980. 'Trophic interactions between astroglial cells and hippocampal neurons in culture', Science, 209: 809-10.
Brennand KJ, et al.: 'Modelling schizophrenia using human induced pluripotent stem cells' Nature. 2011;473:221-225.
Kriks, S. et al: 2011. 'Dopamine neurons derived from human ES cells efficiently engraft in animal models of Parkinson's disease', Nature, 480: 547-51.

* cited by examiner

*Primary Examiner* — Jeremy C Flinders
*Assistant Examiner* — Masudur Rahman
(74) *Attorney, Agent, or Firm* — Christian Cawthorn; NORTON ROSE FULBRIGHT CANADA LLP

(57) ABSTRACT

The present disclosure concerns a cell or tissue culture system comprising a solid support for the culture of adherent cells or adherent tissues and a plurality of cationic dendrimers associated to the surface of the solid support. Each cationic dendrimer includes one or more functional amine group. The cationic dendrimer is protonated at physiological pH. The cell or tissue culture system can be used for the culture of adherent cells or tissues and be used for the differentiation of stem cells.

14 Claims, 53 Drawing Sheets

CATIONIC DENDRIMERS FOR THE CULTURE OF ADHERENT CELLS

CROSS-REFERENCE TO RELATED APPLICATIONS AND DOCUMENTS

This application claims priority on US provisional application 63/219,083, filed Jul. 7, 2021, the entire content of which is hereby incorporated by reference.

TECHNOLOGICAL FIELD

The present disclosure provides culture systems for adherent cells as well as methods for culturing adherent cells.

BACKGROUND

Long-term stable cell culture is a critical tool to better understand cell function. Most adherent cell culture models require a polymer substrate coating of poly-lysine or poly-ornithine for the cells to adhere and survive. However, poly-peptide based substrates are degraded by proteolysis and it remains a challenge to maintain healthy cell cultures for extended periods of time.

Neurons are adherent cells that require an appropriate substrate to survive, differentiate, and elaborate axons and dendrites. In fact, the critical significance of providing an appropriate substrate was identified in the earliest cell culture studies, supporting the conclusion that process extension by adherent cells requires a solid substrate. More contemporary in vitro studies have revealed that depriving adherent cells of a supportive matrix initiates Anoikis, a form of apoptotic cell death triggered by loss of adhesion. While some cells, including many immortalized cell lines, can attach and grow on bare borosilicate glass or tissue culture-treated polystyrene (usually oxidized via oxygen plasma to increase its hydrophobicity, many primary cells, including most neuronal cells, do not sufficiently adhere to the plastic or glass surfaces of cell culture vessels. To adhere and survive, these cells require a more engaging substrate that mimics at least some of the properties of an endogenous extracellular matrix (ECM).

Various ECM components have been employed for this purpose, including collagen, fibronectin, laminins, and ECM extracts like Matrigel™ and/or Geltrex™ to support the attachment and proliferation of neuronal cells, however, these ECM components are expensive to purify and prone to variation in quality. To address these issues, synthetic polypeptides were introduced as a relatively inexpensive alternative to natural ECM components to coat cell culture substrates. Poly-lysine and poly-ornithine are homopolymeric chains of a basic amino acid, that were selected based on early observations that proteins with a high content of positively charged amino acids, such as histones and protamine, adsorbed onto a cell culture substrate would support cell adhesion and proliferation. More recent studies have reported that non-peptide polymers such as polyethyleneimine, polypropyleneimine, polypyrrole, poly(allylguanidine) and poly-electrolyte multilayers (PEMs) can function as substrates to support neural cell culture.

Poly-lysine and poly-ornithine are commonly used as substrate coatings for primary cells and cell lines in contemporary cell culture. The d enantiomer of poly-lysine, poly-d-lysine (PDL) is often preferentially utilized over the l enantiomer, poly-l-lysine (PLL), due to its enhanced resistance to proteases such as trypsin, which improves the stability of the coating in long term cultures. Notably, neuronal cells derived from induced pluripotent stem cells are not sufficiently supported by a polycationic polymer coating alone. To adhere and survive these cells require an additional layer composed of endogenous extracellular matrix (ECM) components, typically Matrigel™ or Geltrex™ or a layer of laminin-1 on top of an initial layer of poly-l-ornithine (PLO).

There is thus a need to provide an improved cell culture system for the culture of pluripotent stem cells.

BRIEF SUMMARY

The present disclosure concerns a cell or tissue culture system allowing the long-term culture of cells or tissues. The cell or tissue culture system comprises a cationic dendrimer designed to associate indirectly or directly with the solid support and the cultured cells/tissues.

According to a first aspect, the present disclosure provides a cell or tissue culture system comprising (i) a solid support for the culture of adherent cells or adherent tissues and (ii) a plurality of cationic dendrimers associated to the surface of the solid support. Each of the cationic dendrimer includes one or more functional amine group and is protonated at physiological pH. In an embodiment, at least 25% of the functional groups of the cationic dendrimer are functional amine groups. In another embodiment, the cationic dendrimers are cationic polyglycerol dendrimers. In a further embodiment, the cationic dendrimers form aggregates on the surface of the solid support. In still another embodiment, the cationic dendrimers are adhered to the surface of the solid support. In some embodiments, the surface of the solid support is substantially planar. In additional embodiments, the solid support comprises glass, plastic (polystyrene for example) or is a combination thereof. In yet another embodiment, the cell or tissue culture system further comprises synthetic polypeptides associated to the surface of the solid support and/or to at least one of the cationic dendrimer. In specific embodiments, the synthetic polypeptides comprise poly-L-lysine and/or poly-D-lysine. In still another embodiment, the cell or tissue culture system further comprises extracellular matrix components, or peptidic fragments thereof such as an RGD peptide, associated to the surface of the solid support and/or to at least one of the cationic dendrimer. In some embodiments, the extracellular matrix components comprise laminin vitrotectin, fibronectin or E-cadherins, or a fragment thereof. In other embodiments, the extracellular matrix components comprise Matrigel™, Geltrex™ or a combination thereof. In a still additional embodiment, the cell or tissue culture further comprises adherent cells. In an embodiment, the adherent cells comprise primary cells. In another embodiment, the adherent cells comprise stem cells. In a further embodiment, the cell or tissue culture system further comprises cells derived from the differentiation of stem cells. In yet another embodiment, the cells derived from the differentiation of stem cells are neurons. In yet a further embodiment, the cells derived from the differentiation of stem cells comprises motor neurons, cortical neurons, dopaminergic neurons and/or hippocampal neurons. In an embodiment, the stem cells comprises undifferentiated pluripotent stem cells, embryonic stem cells and/or progenitor cells. In a further embodiment, the embryonic stem cells are primary embryonic neocortical neurons. In some additional embodiments, the adherent cells comprise immortalized cells. In yet another embodiment, the adherent cells lack the ability to grow on the surface of the solid support in the absence of the plurality of cationic dendrimers associated to the surface of the solid support.

According to a second aspect, the present disclosure provides an in vitro method for culturing adherent cells or adherent tissues. The method comprises contacting adherent cells or adherent tissues with the cell or tissue culture system described herein and a cell culture medium. In an embodiment, the contacting occurs for at least three consecutive days. In still another embodiment, the adherent cells are as defined herein.

According to a third aspect, the present disclosure provides an in vitro method for differentiating stems cells into differentiated cells. The method comprises contacting the stem cells with the cell or tissue culture system described herein, a cell culture medium and a differentiating agent or cocktail. In an embodiment, the contacting occurs for at least three consecutive days. In yet another embodiment, the stem cells and/or the differentiated cells are as defined herein. In still a further embodiment, the method is used for limiting the differentiation of stem cells into glial cells.

According to a fourth aspect, the present disclosure provides a process for making the cell or tissue culture system described herein. The process comprises contacting a solution or a suspension comprising cationic dendrimers with the surface of the solid support so as to cause the association of the plurality of cationic dendrimers to the surface of the solid support. In an embodiment, the solution or the suspension comprises more than 1 µg of the cationic dendrimers per mL and/or at least about 5 µg of the cationic dendrimers per mL. In an embodiment, the contacting occurs at a temperature of at least about 4° C. In still a further embodiment, the contacting occurs for at least about 20 minutes and preferably for at least about 60 minutes.

BRIEF DESCRIPTION OF THE DRAWINGS

Having thus generally described the nature of the invention, reference will now be made to the accompanying drawings, showing by way of illustration, a preferred embodiment thereof, and in which.

µg/mL) of PDL-coated glass coverslips labeled for glial marker S100β (scale bar is 50 µm).

Figure 2A:
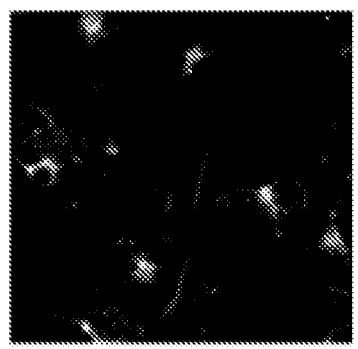
FIG. 2A is a representative photomicrograph of 90 DIV primary rat cortical neurons grown in a concentration of 1 µg/mL) of PDL-coated glass coverslips labeled for nuclear stain Hoechst 33342 (scale bar is 50 µm).
Figure 2B:
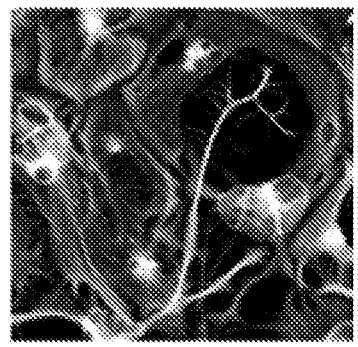
FIG. 2B is a representative photomicrograph of 90 DIV primary rat cortical neurons grown in a concentration of 1 µg/mL) of PDL-coated glass coverslips labeled for glial marker S100β (scale bar is 50 µm).
Figure 2C:
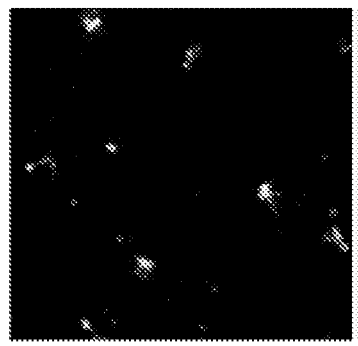
FIG. 2C is a representative photomicrograph of 90 DIV primary rat cortical neurons grown in a concentration of 1 µg/mL) of PDL-coated glass coverslips labeled for NFm (scale bar is 50 µm).
Figure 2D:
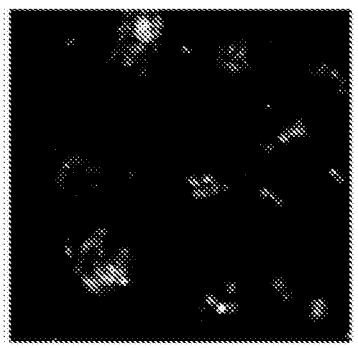
FIG. 2D is a representative photomicrograph of 90 DIV primary rat cortical neurons grown in a concentration of 1 µg/mL) of dPGA-coated glass coverslips labeled for nuclear stain Hoechst 33342 (scale bar is 50 µm).
Figure 2E:
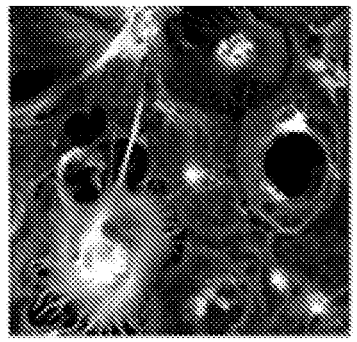
FIG. 2E is a representative photomicrograph of 90 DIV primary rat cortical neurons grown in a concentration of 1 µg/mL) of dPGA-coated glass coverslips labeled for glial marker S100β (scale bar is 50 µm).
Figure 2F:
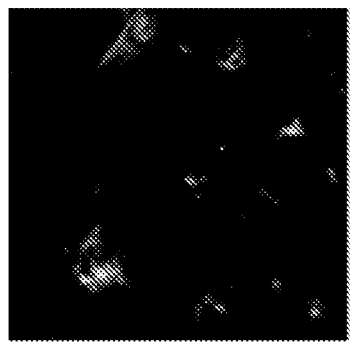
FIG. 2F is a representative photomicrograph of 90 DIV primary rat cortical neurons grown in a concentration of 1 µg/mL) of dPGA-coated glass coverslips labeled for NFm (scale bar is 50 µm).
Figure 2G:
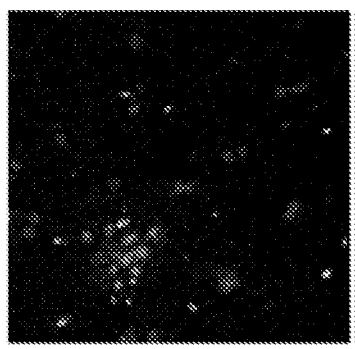
FIG. 2G is a representative photomicrograph of 90 DIV primary rat cortical neurons grown in a concentration of 10 µg/mL) of PDL-coated glass coverslips labeled for nuclear stain Hoechst 33342 (scale bar is 50 µm).
Figure 2H:
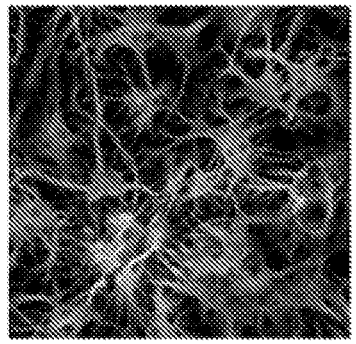
FIG. 2H is a representative photomicrograph of 90 DIV primary rat cortical neurons grown in a concentration of 10
Figure 2I:
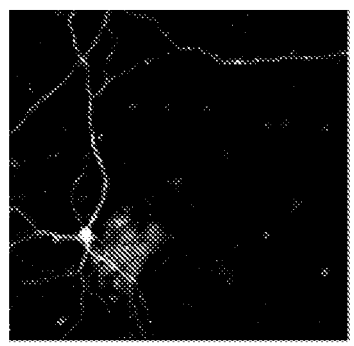

FIG. 2I is a representative photomicrograph of 90 DIV primary rat cortical neurons grown in a concentration of 10 µg/mL) of PDL-coated glass coverslips labeled for NFm (scale bar is 50 µm).

Figure 2J:
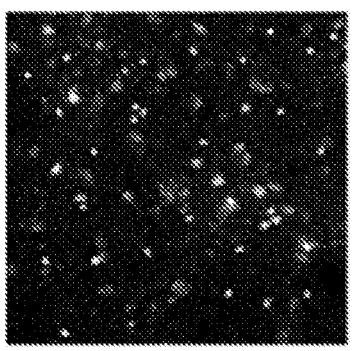

FIG. 2J is a representative photomicrograph of 90 DIV primary rat cortical neurons grown in a concentration of 10 µg/mL) of dPGA-coated glass coverslips labeled for nuclear stain Hoechst 33342 (scale bar is 50 µm).

Figure 2K:
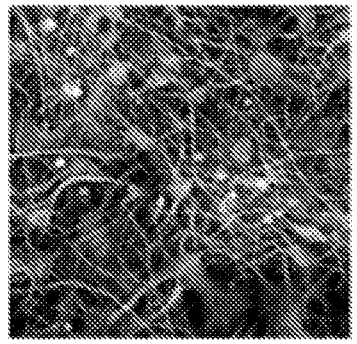

FIG. 2K is a representative photomicrograph of 90 DIV primary rat cortical neurons grown in a concentration of 10 µg/mL) of dPGA-coated glass coverslips labeled for glial marker S100β (scale bar is 50 µm).

Figure 2L:
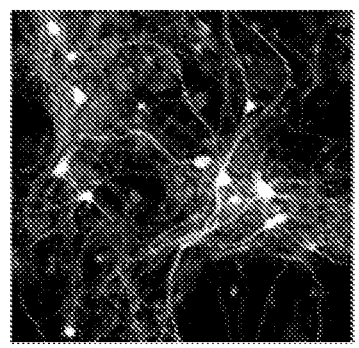

FIG. 2L is a representative photomicrograph of 90 DIV primary rat cortical neurons grown in a concentration of 10 µg/mL) of dPGA-coated glass coverslips labeled for NFm (scale bar is 50 µm).

Figure 2M:
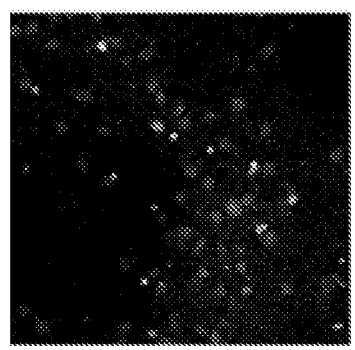

FIG. 2M is a representative photomicrograph of 90 DIV primary rat cortical neurons grown in a concentration of 100 µg/mL) of PDL-coated glass coverslips labeled for nuclear stain Hoechst 33342 (scale bar is 50 µm).

Figure 2N:
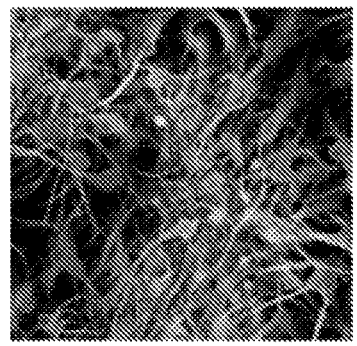

FIG. 2N is a representative photomicrograph of 90 DIV primary rat cortical neurons grown in a concentration of 100 µg/mL) of PDL-coated glass coverslips labeled for glial marker S100β (scale bar is 50 µm).

Figure 2O:
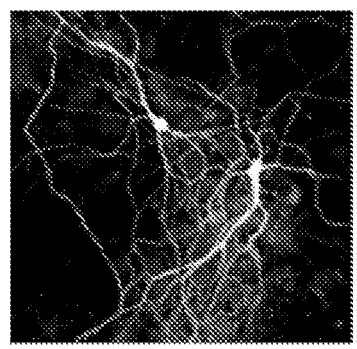

FIG. 2O is a representative photomicrograph of 90 DIV primary rat cortical neurons grown in a concentration of 100 µg/mL) of PDL-coated glass coverslips labeled for NFm (scale bar is 50 µm).

Figure 2P:
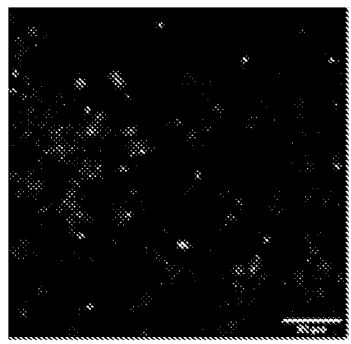

FIG. 2P is a representative photomicrograph of 90 DIV primary rat cortical neurons grown in a concentration of 100 µg/mL) of dPGA-coated glass coverslips labeled for nuclear stain Hoechst 33342 (scale bar is 50 µm).

Figure 2Q:
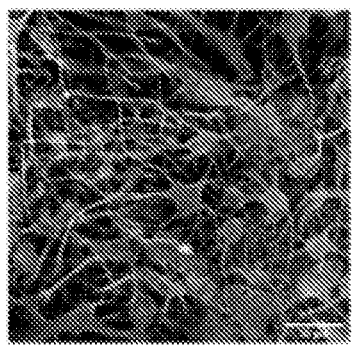

FIG. 2Q is a representative photomicrograph of 90 DIV primary rat cortical neurons grown in a concentration of 100 µg/mL) of dPGA-coated glass coverslips labeled for glial marker S100β (scale bar is 50 µm).

Figure 2R:
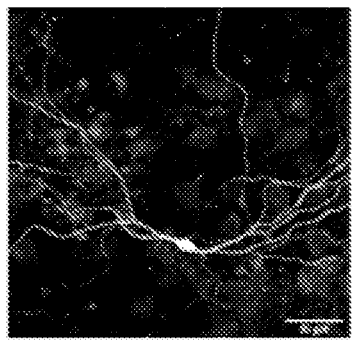

FIG. 2R is a representative photomicrograph of 90 DIV primary rat cortical neurons grown in a concentration of 100 µg/mL) of dPGA-coated glass coverslips labeled for NFm (scale bar is 50 µm).

Figure 2S:
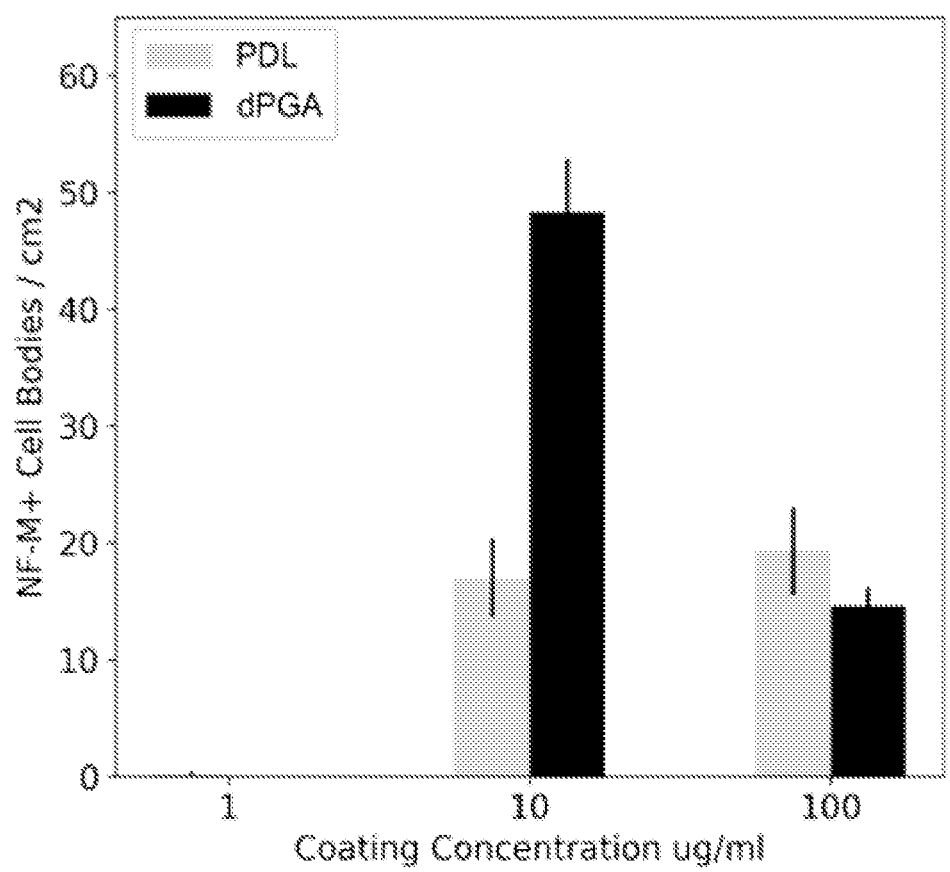

FIG. 2S is a graph showing the quantification of the number of NFm+ positive cells in 90 DIV primary rat cortical cultures grown on glass coverslips treated with increasing concentration (1, 10 or 100 µg/mL) of either PDL or dPGA (* $p<0.05$,  $p<0.01$, * $p<0.001$ paired two-tailed Student's t-test n=10).

Figure 2T:
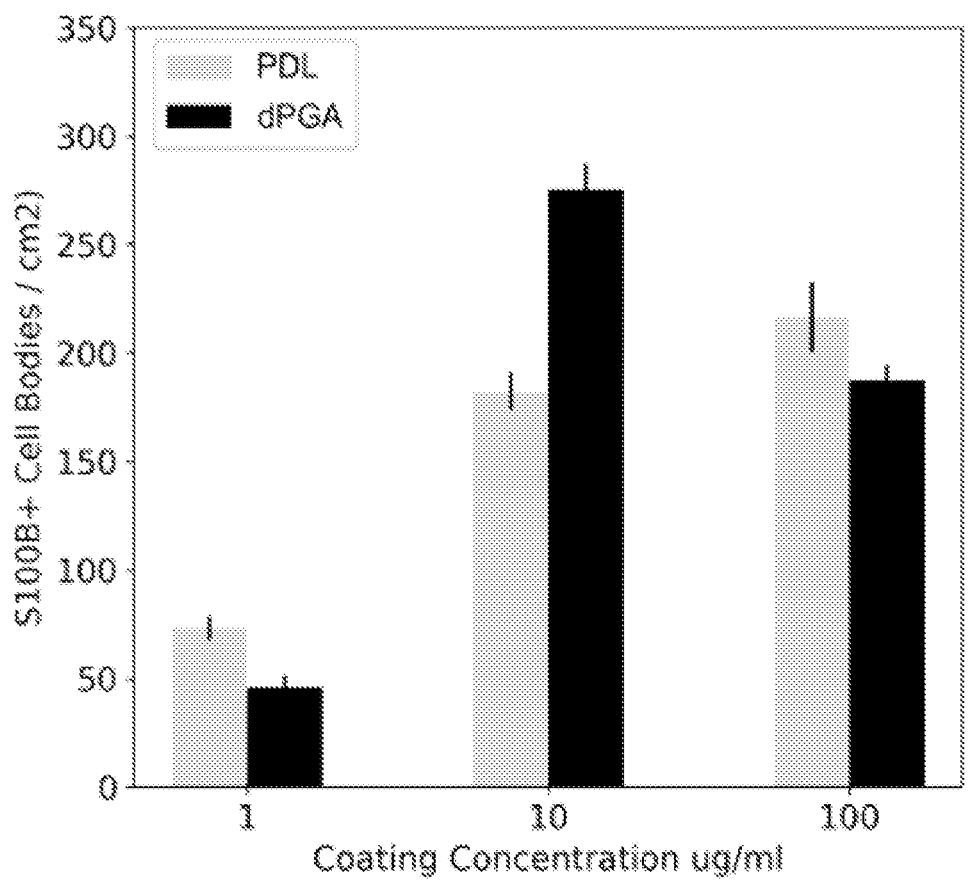

FIG. 2T is a graph showing the quantification of the number of S100β positive cells of 90 DIV primary rat cortical cultures grown on glass coverslips treated with increasing concentration (1, 10 or 100 µg/mL) of either PDL or dPGA (* $p<0.05$,  $p<0.01$, * $p<0.001$ paired two-tailed Student's t-test n=10).

Figure 3A:
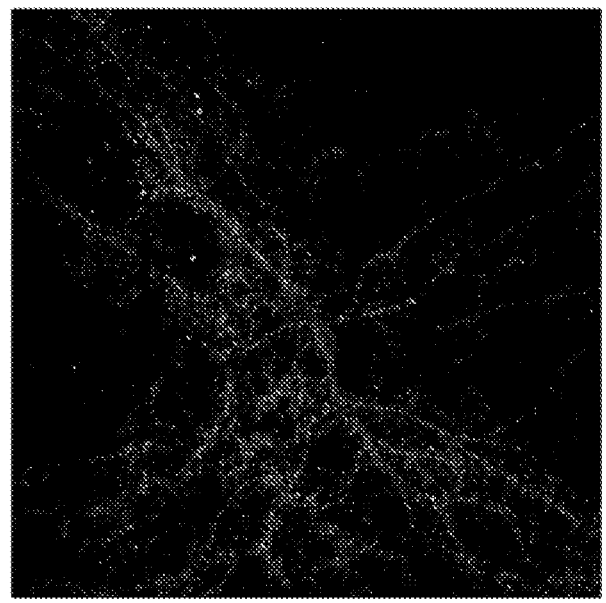

FIG. 3A is a representative image of rat primary cortical neurons after 3 months of culture on glass coverslips coated with 10 µg/ml of PDL. The culture was labeled with antibodies against postsynaptic marker PSD95.

Figure 3B:
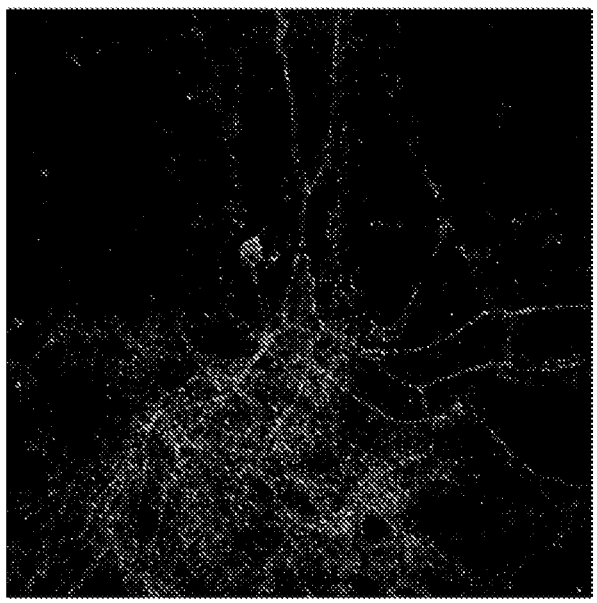

FIG. 3B is a representative image of rat primary cortical neurons after 3 months of culture on glass coverslips coated with 10 µg/ml of pDGA. The culture was labeled with antibodies against postsynaptic marker PSD95.

Figure 3C:
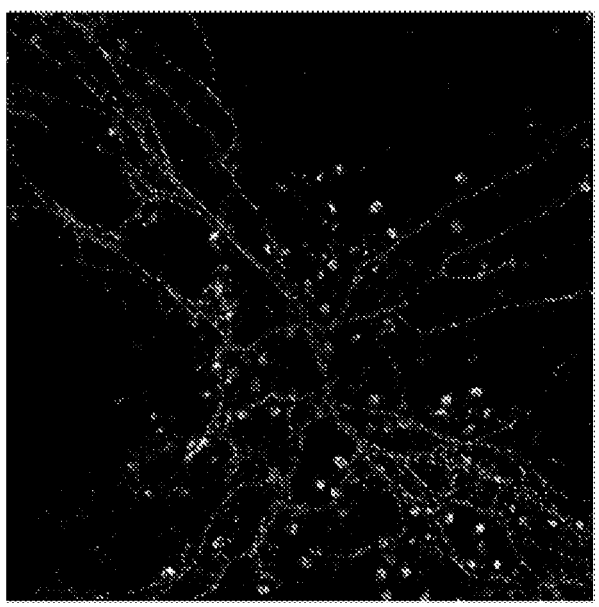

FIG. 3C is a representative image of rat primary cortical neurons after 3 months of culture on glass coverslips coated with 10 µg/ml of PDL. The culture was labeled with antibodies against presynaptic marker Synaptophysin 1 (Synp).

Figure 3D:
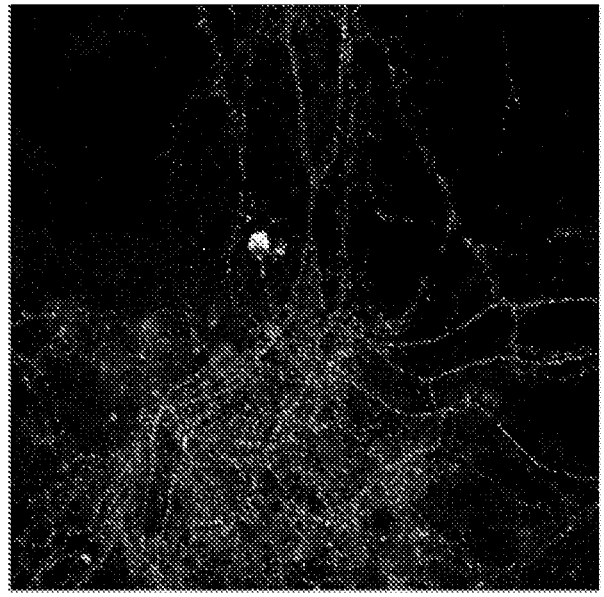

FIG. 3D is a representative image of rat primary cortical neurons after 3 months of culture on glass coverslips coated with 10 µg/ml of pDGA. The culture was labeled with antibodies against presynaptic marker Synaptophysin 1 (Synp).

Figure 3E:
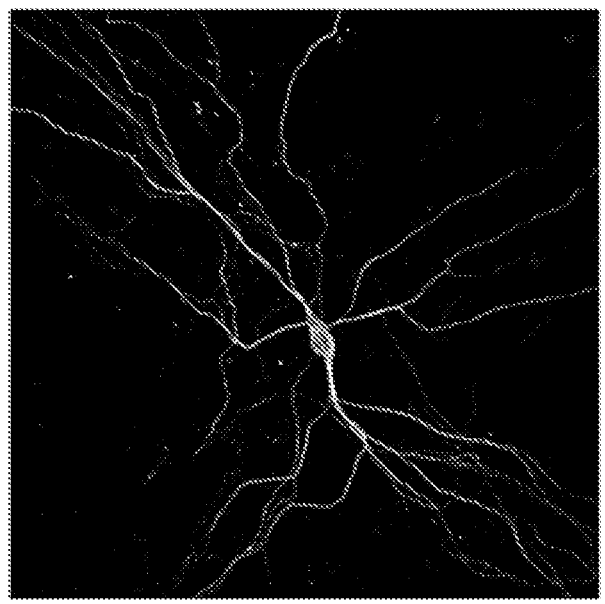

FIG. 3E is a representative image of rat primary cortical neurons after 3 months of culture on glass coverslips coated with 10 µg/ml of PDL. The culture was labeled with antibodies against neuron specific marker Class III β-tubulin (Tubb3).

Figure 3F:
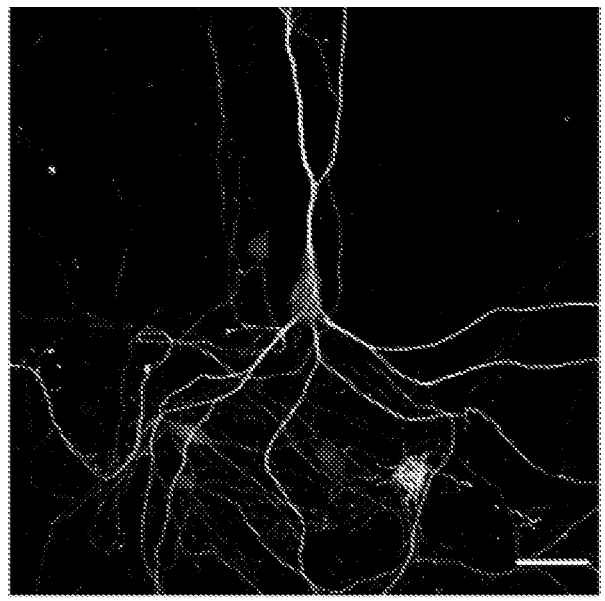

FIG. 3F is a representative image of rat primary cortical neurons after 3 months of culture on glass coverslips coated with 10 µg/ml of pDGA. The culture was labeled with antibodies against neuron specific marker Class III β-tubulin (Tubb3).

Figure 4A:
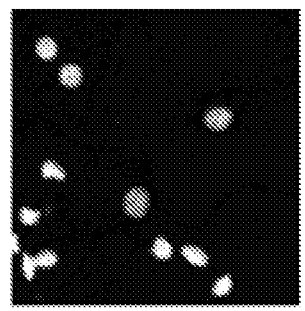

FIG. 4A shows a micrograph of embryonic rat primary cortical neuron cultures at 12 DIV grown on coverslips coated with 100 µg/ml of PDL and stained with Hoechst 33342 dye (Hoechst) (scale bar 20 µm).

Figure 4B:
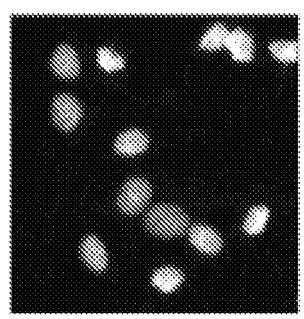

FIG. 4B shows a micrograph of embryonic rat primary cortical neuron cultures at 12 DIV grown on coverslips coated with 100 µg/ml of dPGA and stained with Hoechst 33342 dye (Hoechst) (scale bar 20 µm).

Figure 4C:
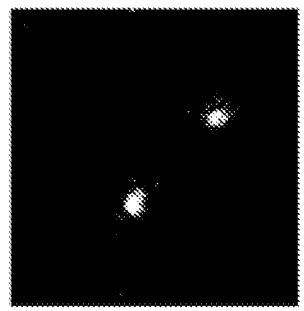

FIG. 4C shows a micrograph of embryonic rat primary cortical neuron cultures at 12 DIV grown on coverslips coated with 100 µg/ml of PDL and labeled for neuronal markers NeuN (scale bar 20 µm).

Figure 4D:
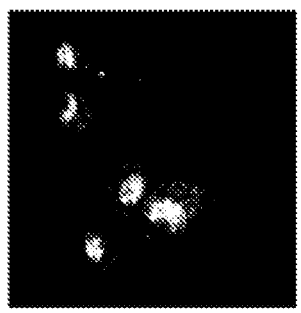

FIG. 4D shows a micrograph of embryonic rat primary cortical neuron cultures at 12 DIV grown on coverslips coated with 100 µg/ml of dPGA and labeled for neuronal markers NeuN (scale bar 20 µm).

Figure 4E:
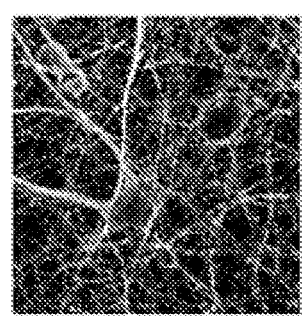

FIG. 4E shows a micrograph of embryonic rat primary cortical neuron cultures at 12 DIV grown on coverslips coated with 100 µg/ml of PDL and labeled for Beta-3-tubulin (Tubb3) (scale bar 20 µm).

Figure 4F:
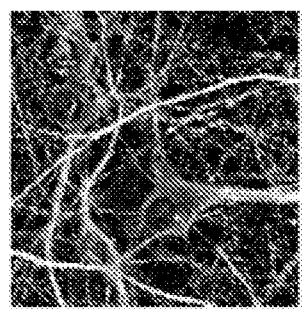

FIG. 4F shows a micrograph of embryonic rat primary cortical neuron cultures at 12 DIV grown on coverslips coated with 100 µg/ml of dPGA and labeled for Beta-3-tubulin (Tubb3) (scale bar 20 µm).

Figure 4G:
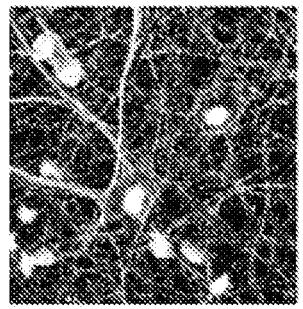

FIG. 4G is a micrograph showing the merged images of FIGS. 4A, 4C, and 4E.

Figure 4H:
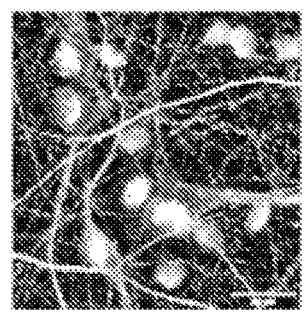

FIG. 4H is a micrograph showing the merged images of FIGS. 4B, 4D, and 4F.

Figure 4I:
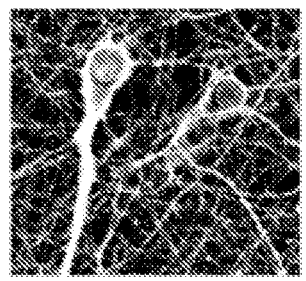

FIG. 4I is a micrograph of primary rat cortical neuron cultures at 12 DIV grown on coverslips coated with 100 µg/ml of PDL and labeled for neuronal markers NFm (scale bar 20 µm).

Figure 4J:
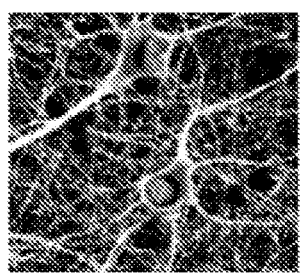

FIG. 4J is a micrograph of primary rat cortical neuron cultures at 12 DIV grown on coverslips coated with 100 µg/ml of dPGA and labeled for neuronal markers NFm (scale bar 20 µm).

Figure 4K:
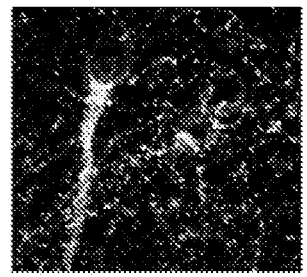

FIG. 4K is a micrograph of primary rat cortical neuron cultures at 12 DIV grown on coverslips coated with 100 µg/ml of PDL and labeled for Synp (scale bar 20 µm).

Figure 4L:
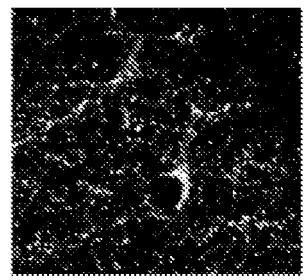

FIG. 4L is a micrograph of primary rat cortical neuron cultures at 12 DIV grown on coverslips coated with 100 µg/ml of dPGA and labeled for Synp (scale bar 20 µm).

Figure 4M:
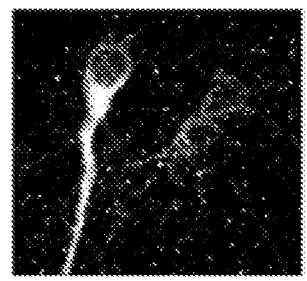

FIG. 4M is a micrograph of primary rat cortical neuron cultures at 12 DIV grown on coverslips coated with 100 µg/ml of PDL and labeled for PSD-95 (scale bar 20 µm).

Figure 4N:
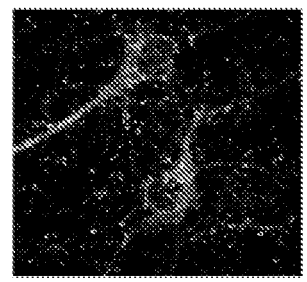

FIG. 4N is a micrograph of primary rat cortical neuron cultures at 12 DIV grown on coverslips coated with 100 µg/ml of dPGA and labeled for PSD-95 (scale bar 20 µm).

Figure 4O:
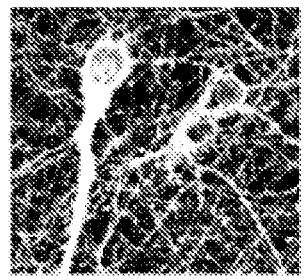

FIG. 4O is a micrograph showing the merged images of FIGS. 4I, 4K, and 4M.

Figure 4P:
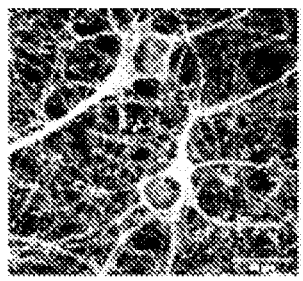

FIG. 4P is a micrograph showing the merged images of FIGS. 4J, 4L, and 4N.

Figure 4Q:
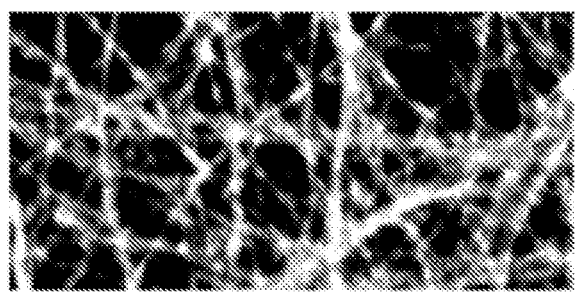

FIG. 4Q shows a higher magnification micrograph of primary rat cortical neuron cultures at 12 DIV grown on coverslips coated with 100 µg/ml of PDL and labeled for neuronal markers NFm (scale bar 2 µm).

Figure 4R:
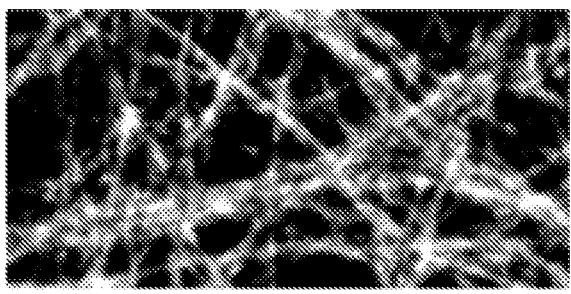

FIG. 4R shows a higher magnification micrograph of primary rat cortical neuron cultures at 12 DIV grown on coverslips coated with 100 µg/ml of dPGA and labeled for neuronal markers NFm (scale bar 2 µm).

Figure 4S:
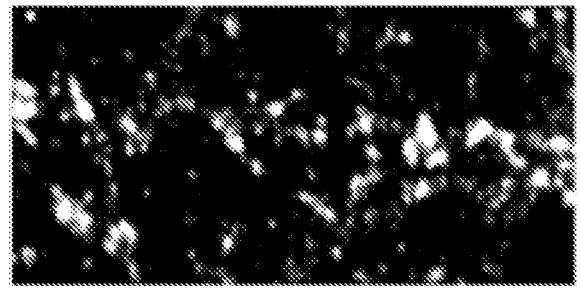

FIG. 4S shows a higher magnification micrograph of primary rat cortical neuron cultures at 12 DIV grown on coverslips coated with 100 µg/ml of PDL and labeled for Synp (scale bar 2 µm).

Figure 4T:
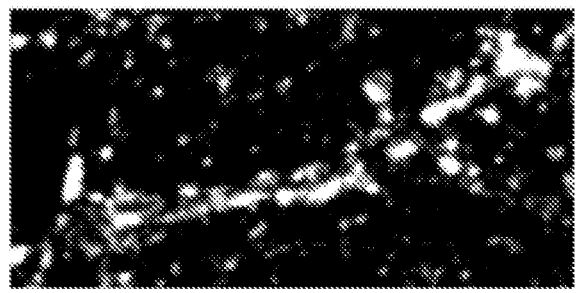

FIG. 4T shows a higher magnification micrograph of primary rat cortical neuron cultures at 12 DIV grown on coverslips coated with 100 µg/ml of dPGA and labeled for Synp (scale bar 2 µm).

Figure 4U:
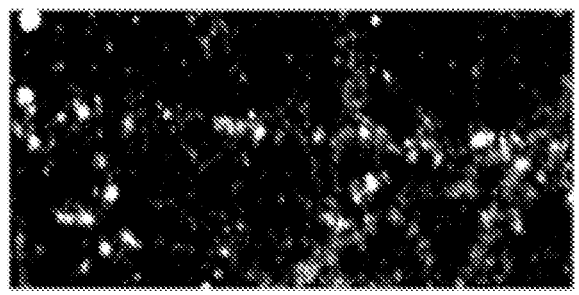

FIG. 4U shows a higher magnification micrograph of primary rat cortical neuron cultures at 12 DIV grown on coverslips coated with 100 µg/ml of PDL and labeled for PDS-95 (scale bar 2 µm).

Figure 4V:
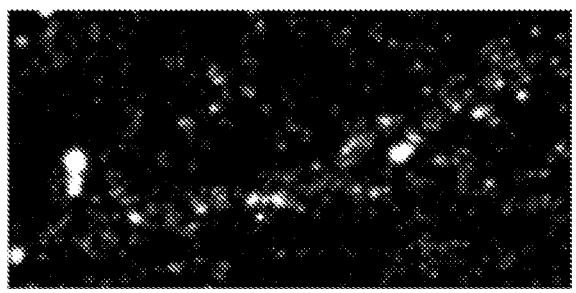

FIG. 4V shows a higher magnification micrograph of primary rat cortical neuron cultures at 12 DIV grown on coverslips coated with 100 µg/ml of dPGA and labeled for neuronal markers PDS-95 (scale bar 2 µm).

Figure 4W:
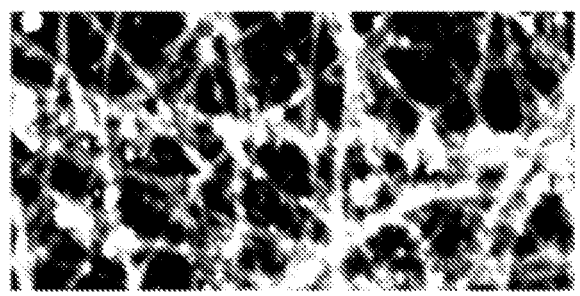

FIG. 4W is a micrograph showing the merged images of FIGS. 4Q, 4S, and 4U.

Figure 4X:
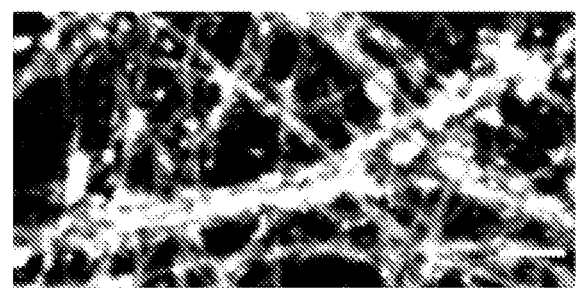

FIG. 4X is a micrograph showing the merged images of FIGS. 4R, 4T, and 4V.

Figure 5A:
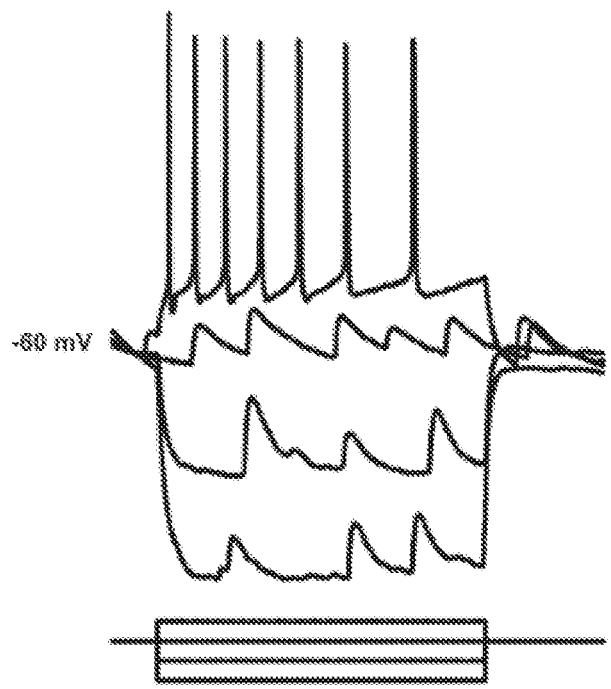

FIG. 5A shows a representative membrane potential traces from patch clamp recordings (primary cortical neurons grown on surfaces coated with PDL) following current injection.

Figure 5B:
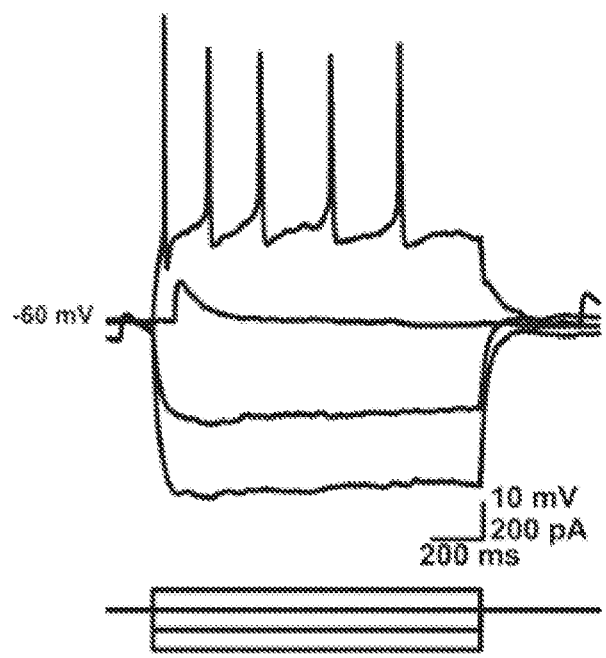

FIG. 5B shows a representative membrane potential traces from patch clamp recordings (primary cortical neurons grown on surfaces coated with dPGA) following current injection.

Figure 5C:
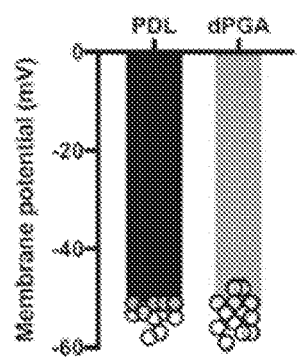

FIG. 5C is a graph showing a comparison of the resting membrane potential (primary cortical neurons grown on surfaces coated with PDL vs. dPGA).

Figure 5D:
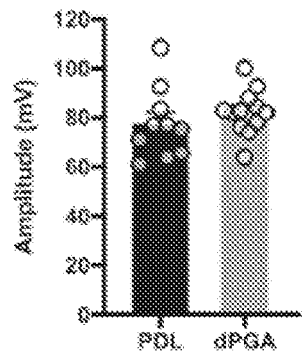

FIG. 5D is a graph showing a comparison of the amplitude of action potentials (primary cortical neurons grown on surfaces coated with PDL vs. dPGA).

Figure 5E:
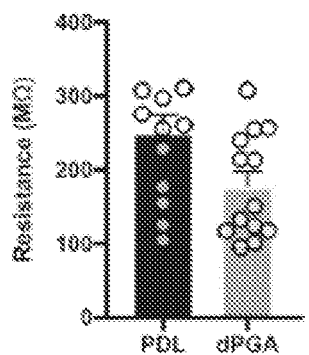

FIG. 5E is a graph showing a comparison of the membrane resistance (primary cortical neurons grown on surfaces coated with PDL vs. dPGA).

Figure 5F:
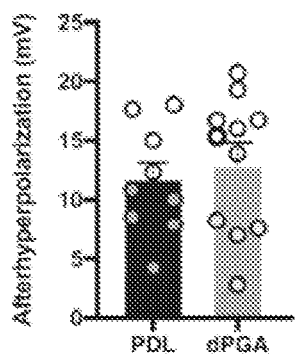

FIG. 5F is a graph showing a comparison of after-hyperpolarization amplitude (primary cortical neurons grown on surfaces coated with PDL vs. dPGA).

Figure 5G:
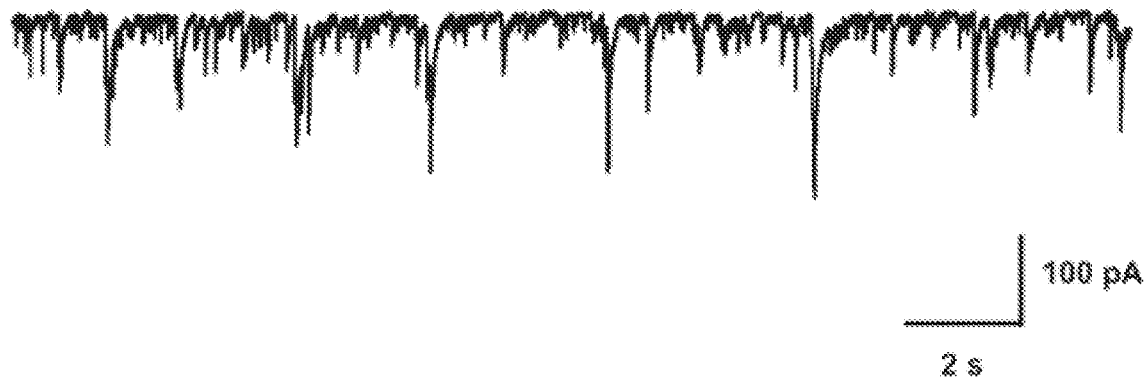

FIG. 5G shows representative traces of synaptic excitatory post-synaptic currents (sEPSCs) recorded while cells were maintained at −70 mV for primary cortical neurons grown on surfaces coated with PDL.

Figure 5H:
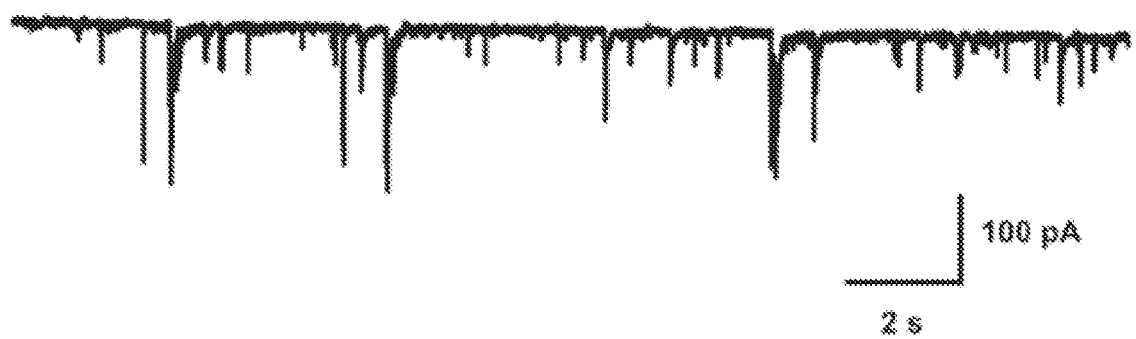

FIG. 5H shows representative traces of synaptic excitatory post-synaptic currents (sEPSCs) recorded while cells were maintained at −70 mV for primary cortical neurons grown on surfaces coated with dPGA.

Figure 5I:
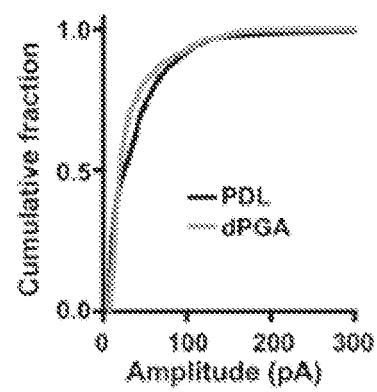

FIG. 5I is a graph showing a comparison (cumulative fraction) of spontaneous excitatory postsynaptic current (sEPSC) amplitude (primary cortical neurons grown on surfaces coated with PDL vs. dPGA).

Figure 5J:
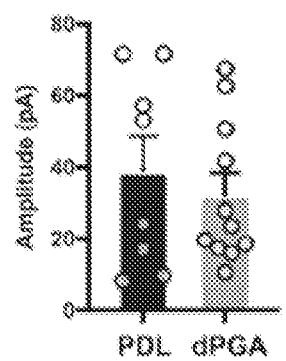

FIG. 5J is a graph showing a comparison (bar graph) of spontaneous excitatory postsynaptic current (sEPSC) amplitude (primary cortical neurons grown on surfaces coated with PDL vs. dPGA).

Figure 5K:
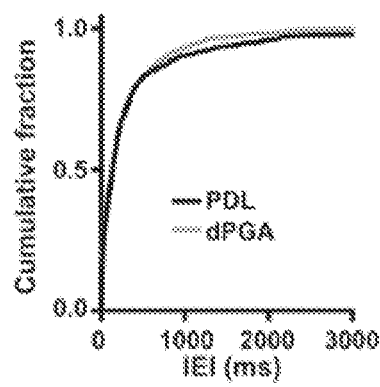

FIG. 5K is a graph showing a comparison (cumulative fraction) of the sEPSC frequency (primary cortical neurons grown on surfaces coated with PDL vs. dPGA).

Figure 5L:
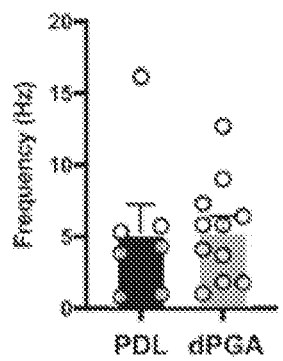

FIG. 5L is a graph showing a comparison (bar graph) of the sEPSC frequency (primary cortical neurons grown on surfaces coated with PDL vs. dPGA).

Figure 5M:
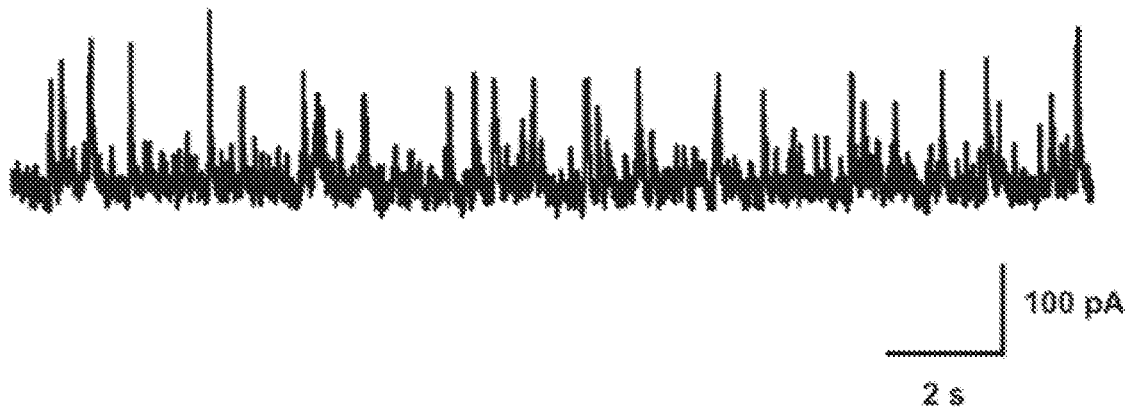

FIG. 5M is a representative traces of synaptic inhibitory post-synaptic currents (sIPSCs) recorded while cells were maintained at −0 mV (primary cortical neurons grown on surfaces coated with PDL).

Figure 5N:
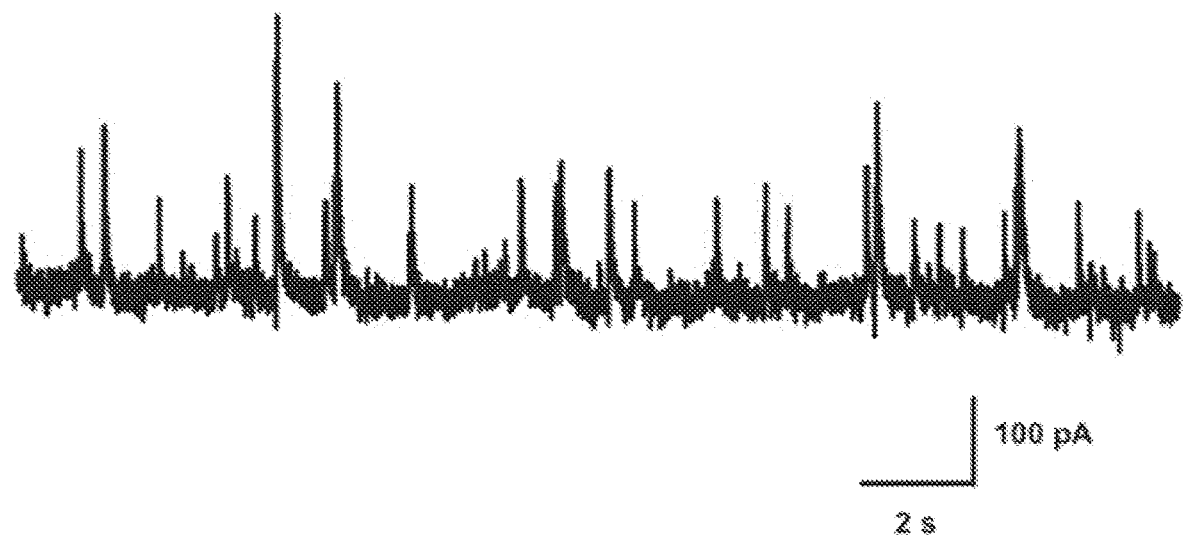

FIG. 5N is a representative traces of synaptic inhibitory post-synaptic currents (sIPSCs) recorded while cells were maintained at −0 mV (primary cortical neurons grown on surfaces coated with pDGA).

Figure 5O:
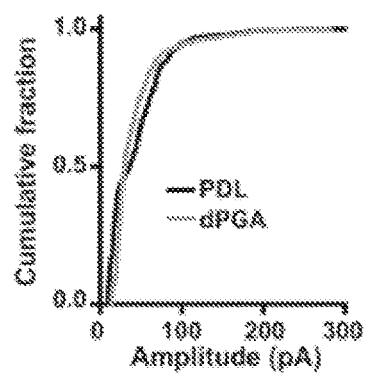

FIG. 5O is a graph showing a comparison (cumulative fraction) of the sIPSC amplitude (primary cortical neurons grown on surfaces coated with PDL vs. dPGA).

Figure 5P:
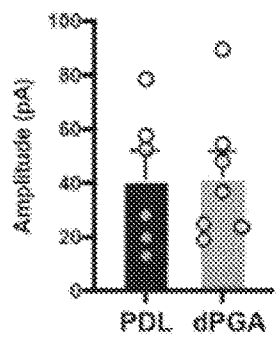

FIG. 5P is a graph showing a comparison (bar graph) of the sIPSC amplitude (primary cortical neurons grown on surfaces coated with PDL vs. dPGA).

Figure 5Q:
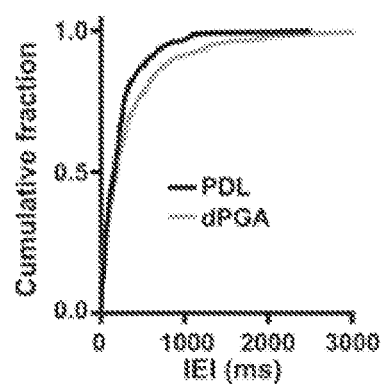

FIG. 5Q is a graph showing a comparison (cumulative fraction) of the sIPSC frequency (primary cortical neurons grown on surfaces coated with PDL vs. dPGA).

Figure 5R:
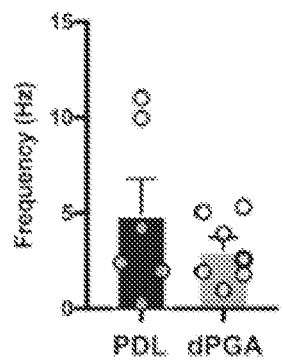

FIG. 5R is a graph showing a comparison (bar graph) of the sIPSC frequency (primary cortical neurons grown on surfaces coated with PDL vs. dPGA).

Figure 6A:
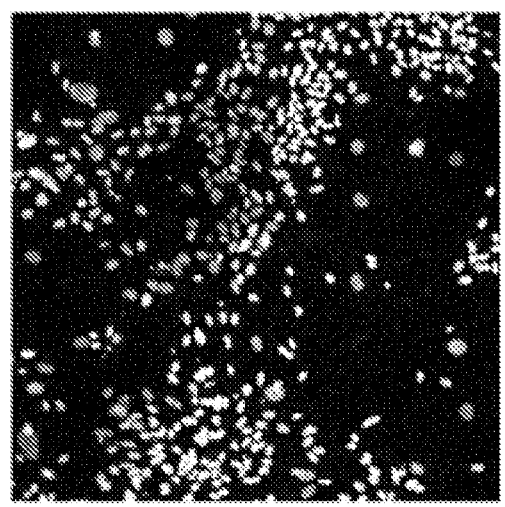

FIG. 6A is a representative photomicrograph of 2 week-old hiPSC-derived cortical neuron cultures grown on a PLO-laminin surface and stained with a nuclear dye Hoechst 33342 (Hoechst) (scale bar 100 µm).

Figure 6B:
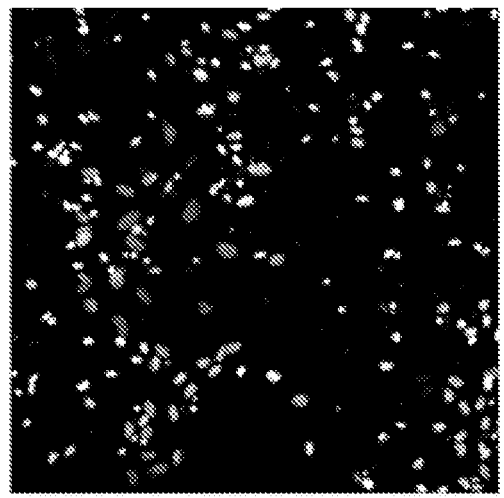

FIG. 6B is a representative photomicrograph of 2 week-old hiPSC-derived cortical neuron cultures grown on a dPGA-laminin surface and stained with a nuclear dye Hoechst 33342 (Hoechst) (scale bar 100 µm).

Figure 6C:
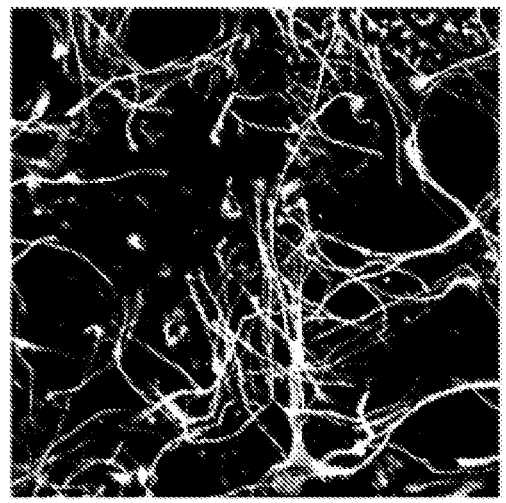

FIG. 6C is a representative photomicrograph of 2 week-old hiPSC-derived cortical neuron cultures grown on a PLO-laminin surface and stained with antibodies against Tubb3 (scale bar 100 µm).

Figure 6D:
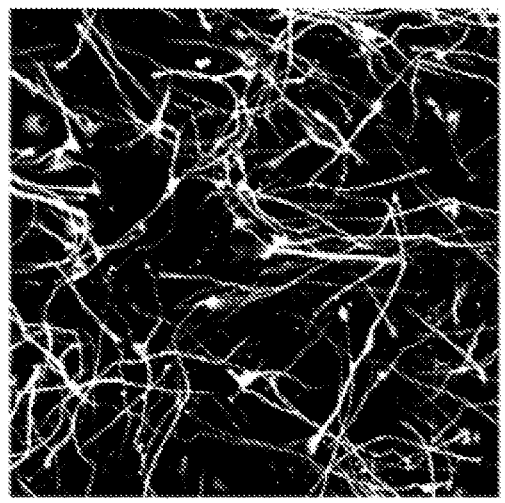

FIG. 6D is a representative photomicrograph of 2 week-old hiPSC-derived cortical neuron cultures grown on a dPGA-laminin surface and stained with antibodies against Tubb3 (scale bar 100 µm).

Figure 6E:
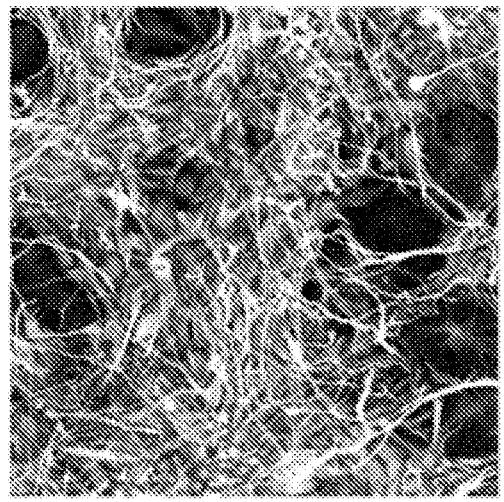

FIG. 6E is a representative photomicrograph of 2 week-old hiPSC-derived cortical neuron cultures grown on a PLO-laminin surface and stained with antibodies against S100B (scale bar 100 µm).

Figure 6F:
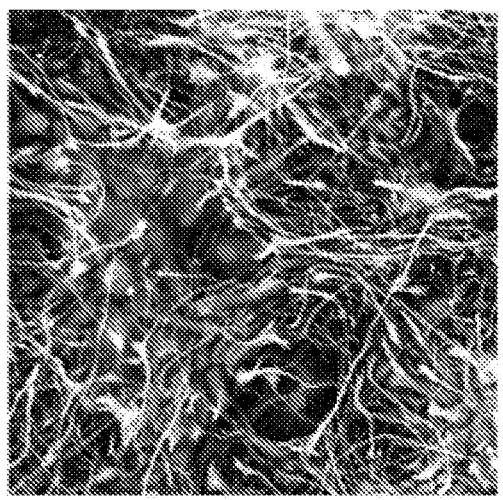

FIG. 6F is a representative photomicrograph of 2 week-old hiPSC-derived cortical neuron cultures grown on a dPGA-laminin surface and stained with antibodies against S100B (scale bar 100 µm).

Figure 6G:
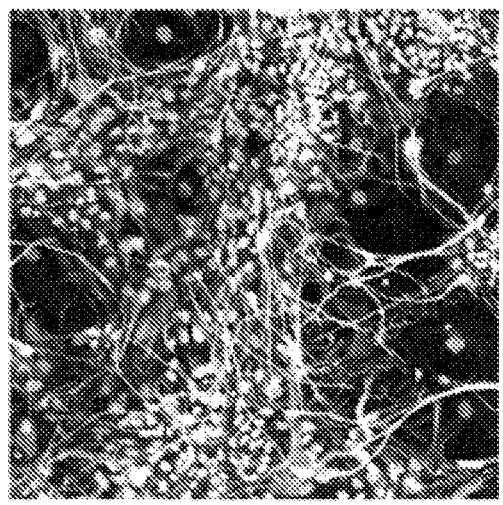

FIG. 6G is a photomicrograph showing the merger of FIGS. 6A, 6C and 6E.

Figure 6H:
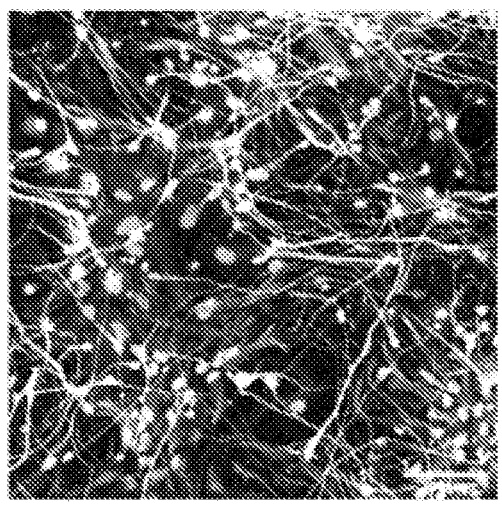

FIG. 6H is a photomicrograph showing the merger of FIGS. 6B, 6D and 6F.

Figure 6I:
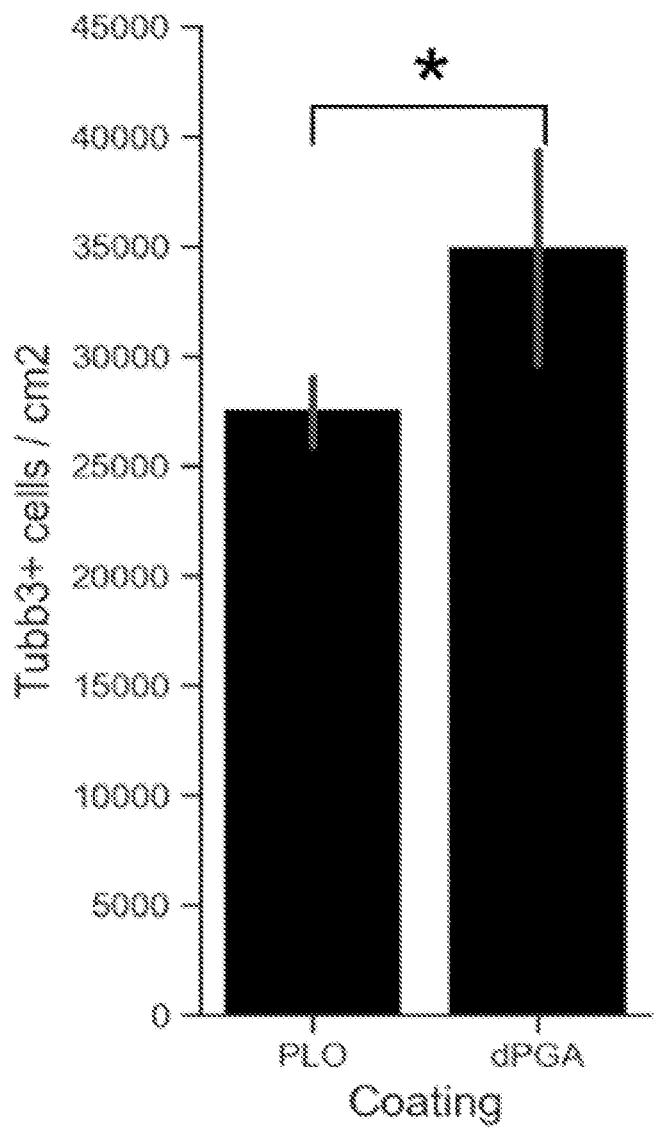

FIG. 6I is a graph showing the quantification of the number of Beta-3 Tubulin+ positive cells in 2 week-old hiPSC-derived cortical neuron cultures grown on a PLO-laminin or a dPGA-laminin (* $p<0.05$, ** $p<0.01$, paired two-tails Student's t-test n=6).

Figure 6J:
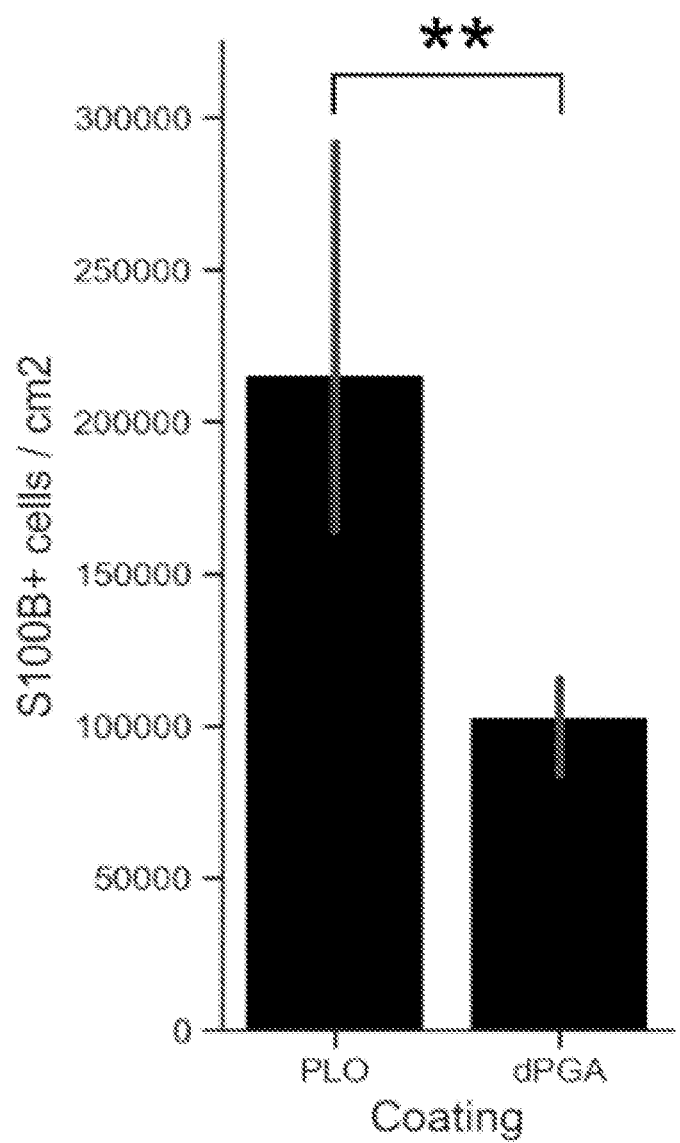

FIG. 6J is a graph showing the quantification of the number of S100β cells (middle) in 2 week-old hiPSC-derived cortical neuron cultures grown on a PLO-laminin or a dPGA-laminin (* $p<0.05$, ** $p<0.01$, paired two-tails Student's t-test n=6).

Figure 6K:
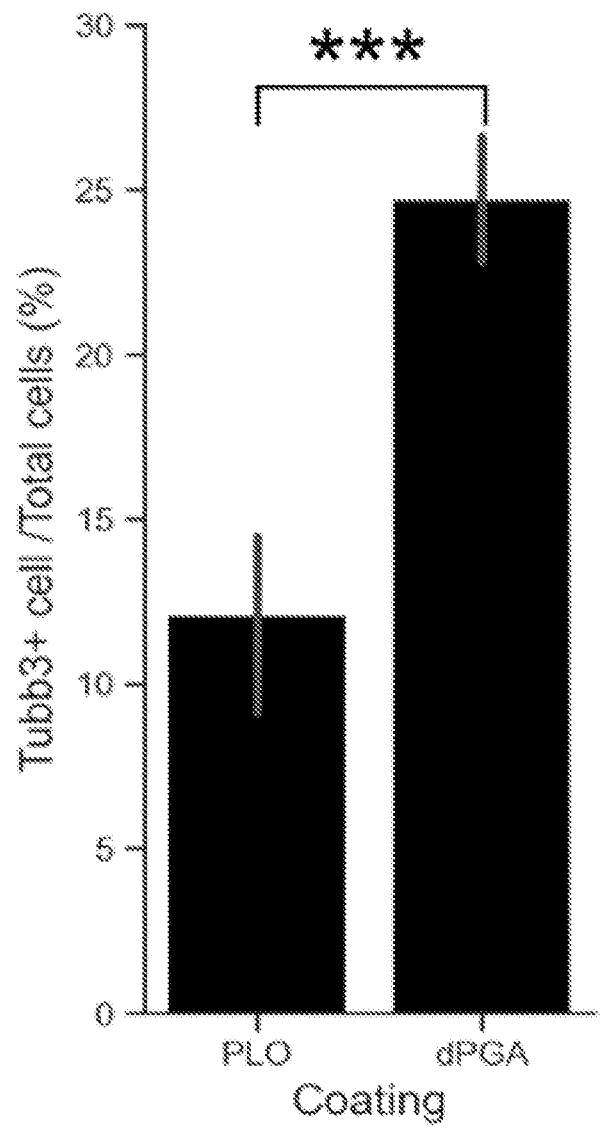

FIG. 6K is a graph showing the quantification of the percentage of Tubb3+ neurons to the total number of cells in 2 week-old hiPSC-derived cortical neuron cultures grown on a PLO-laminin or a dPGA-laminin (* $p<0.05$, ** $p<0.01$, paired two-tails Student's t-test n=6).

Figure 7A:
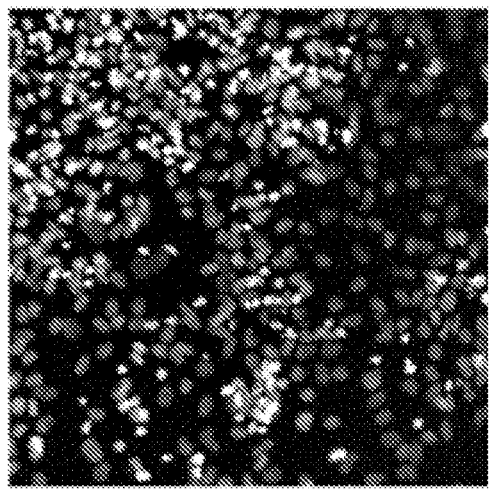

FIG. 7A is a representative micrograph of 2 weeks-old hiPSC-derived dopaminergic neuron cultures grown on a PLO-laminin coated surfaces and stained with the nuclear dye Hoechst 33342 (Hoechst) (scale bar 50 um).

Figure 7B:
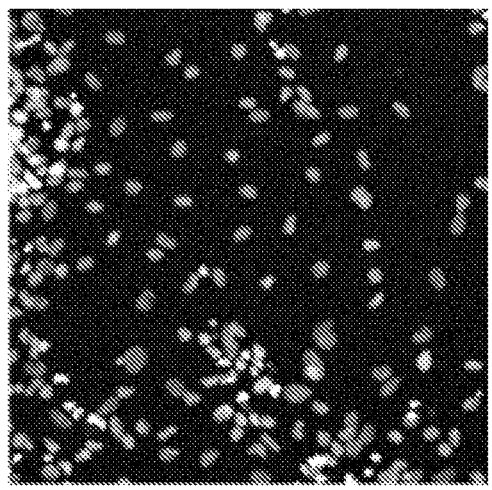

FIG. 7B is a representative micrograph of 2 weeks-old hiPSC-derived dopaminergic neuron cultures grown on a dPGA-laminin coated surfaces and stained with the nuclear dye Hoechst 33342 (Hoechst) (scale bar 50 um).

Figure 7C:
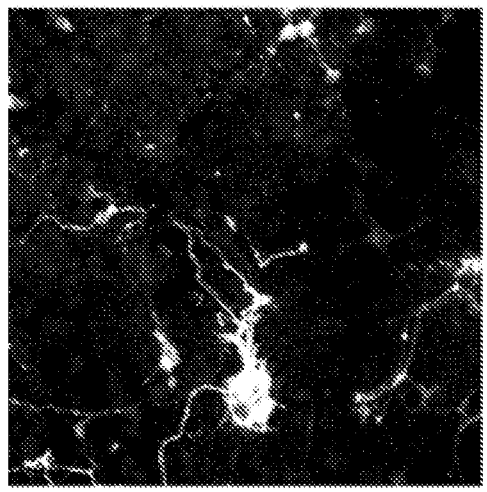

FIG. 7C is a representative micrograph of 2 weeks-old hiPSC-derived dopaminergic neuron cultures grown on a PLO-laminin coated surfaces and stained with antibodies against the dopaminergic neuronal marker Tyrosine hydroxylase (TH) (scale bar 50 um).

Figure 7D:
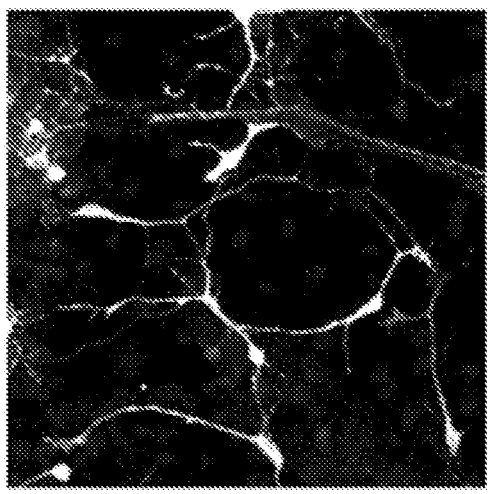

FIG. 7D is a representative micrograph of 2 weeks-old hiPSC-derived dopaminergic neuron cultures grown on a dPGA-laminin coated surfaces and stained with antibodies against the dopaminergic neuronal marker Tyrosine hydroxylase (TH) (scale bar 50 um).

Figure 7E:
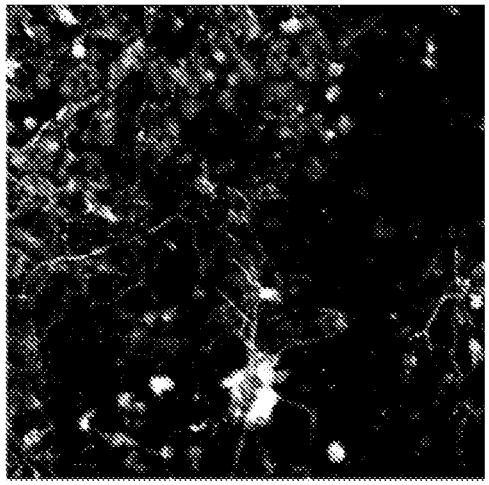

FIG. 7E is a representative micrograph of 2 weeks-old hiPSC-derived dopaminergic neuron cultures grown on a PLO-laminin coated surfaces and stained with antibodies against Tubb3 (scale bar 50 um).

Figure 7F:
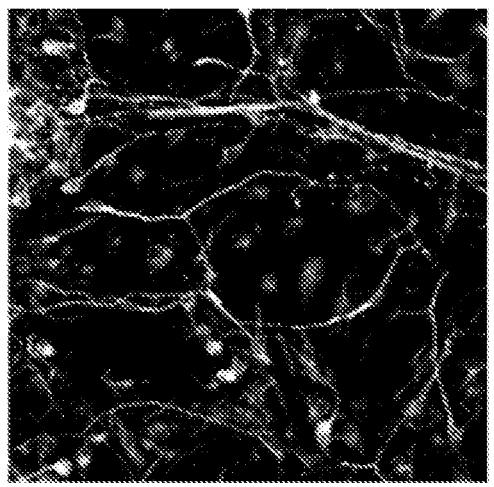

FIG. 7F is a representative micrograph of 2 weeks-old hiPSC-derived dopaminergic neuron cultures grown on a dPGA-laminin coated surfaces and stained with antibodies against Tubb3 (scale bar 50 um).

Figure 7G:

FIG. 7G is a photomicrograph showing the merger of FIGS. 7A, 7C and 7E.

Figure 7H:
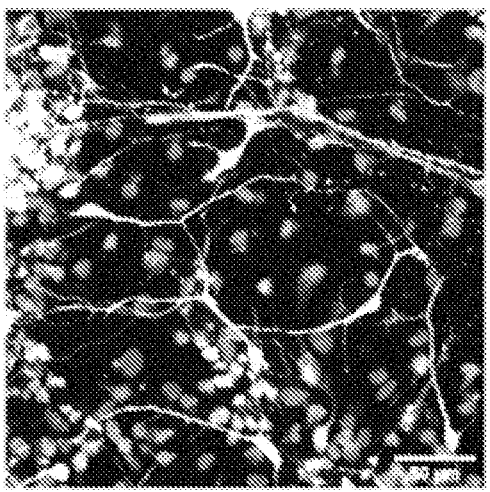

FIG. 7H is a photomicrograph showing the merger of FIGS. 7B, 7D and 7F.

Figure 7I:
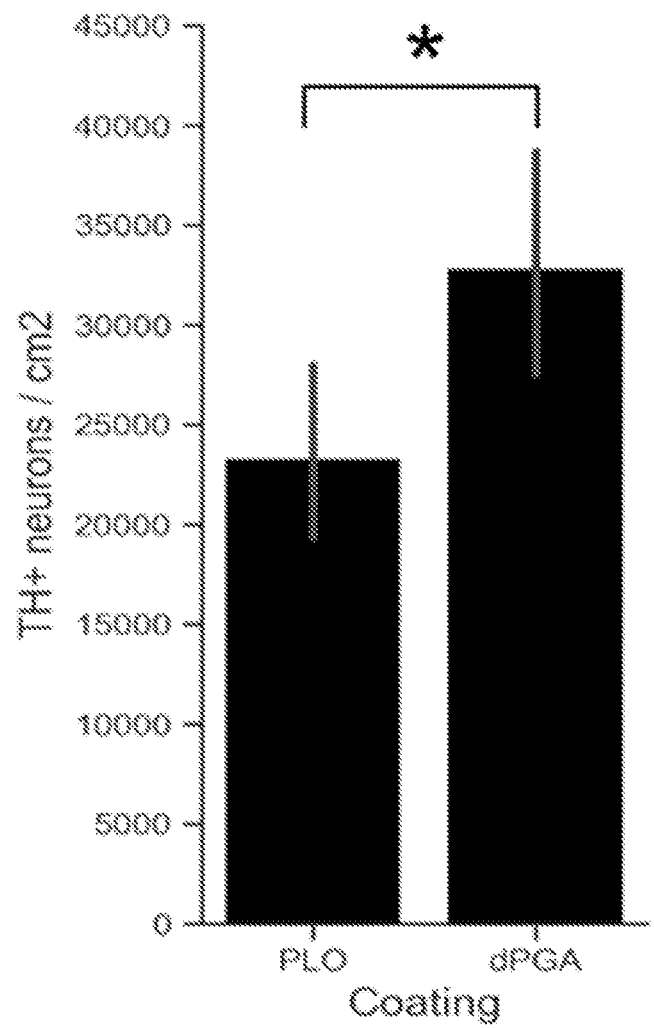

FIG. 7I is a graph showing the quantification of the number of TH+ positive cells in 2 weeks-old hiPSC-derived dopaminergic neuron cultures grown on a PLO-laminin or a DPGA-laminin (* $p<0.05$, ** $p<0.01$, paired two-tailed Student's t-test n=6).

Figure 7J:
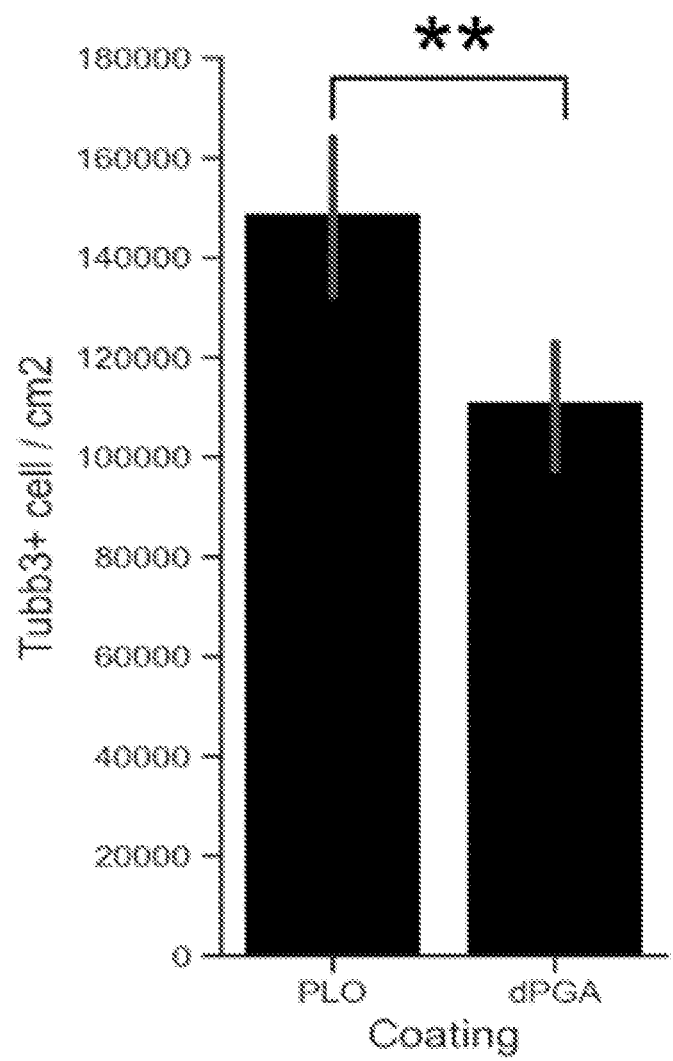

FIG. 7J is a graph showing the quantification of the number of Tubb3+ cells in 2 weeks-old hiPSC-derived dopaminergic neuron cultures grown on a PLO-laminin or a DPGA-laminin (* $p<0.05$, ** $p<0.01$, paired two-tailed Student's t-test n=6).

Figure 7K:
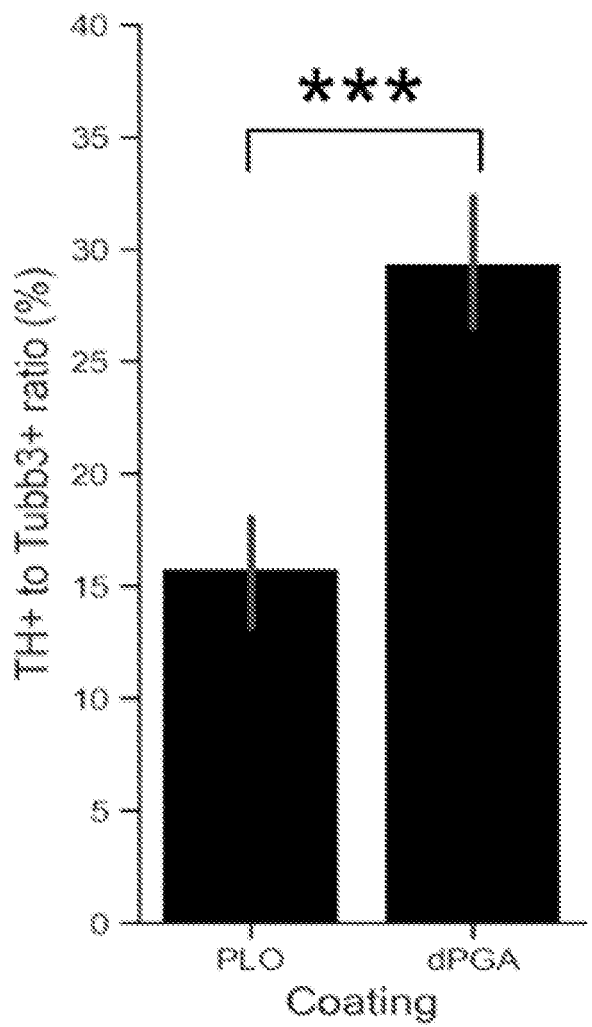

FIG. 7K is a graph showing the quantification of the percentage of TH+ neurons to the total number of Tubb3+ neurons in 2 weeks-old hiPSC-derived dopaminergic neuron cultures grown on a PLO-laminin or a DPGA-laminin (* $p<0.05$, ** $p<0.01$, paired two-tailed Student's t-test n=6).

Figure 8A:
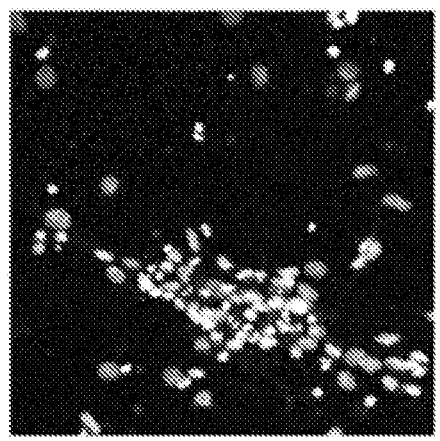

FIG. 8A shows a representative micrograph of 4 week-old hiPSC-derived hippocampal neuron cultures grown on a PLO-laminin surface and stained with a nuclear dye (Hoechst 33342 (Hoechst) (scale bar 50 um).

Figure 8B:
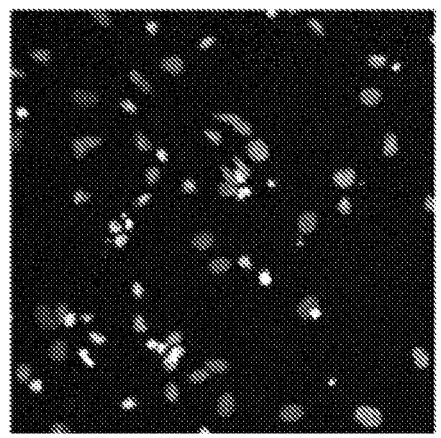

FIG. 8B shows a representative micrograph of 4 week-old hiPSC-derived hippocampal neuron cultures grown on a dPGA-laminin surface and stained with a nuclear dye (Hoechst 33342 (Hoechst) (scale bar 50 um).

Figure 8C:
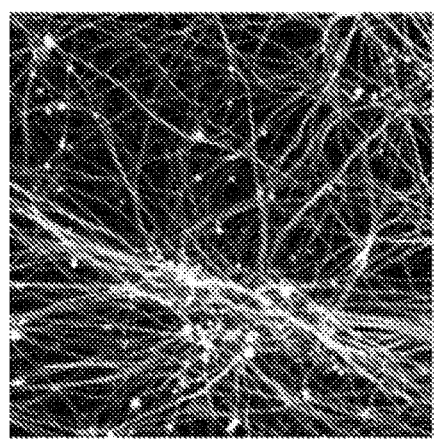

FIG. 8C shows a representative micrograph of 4 week-old hiPSC-derived hippocampal neuron cultures grown on a PLO-laminin surface and stained with antibodies against Tubb3 (scale bar 50 um).

Figure 8D:
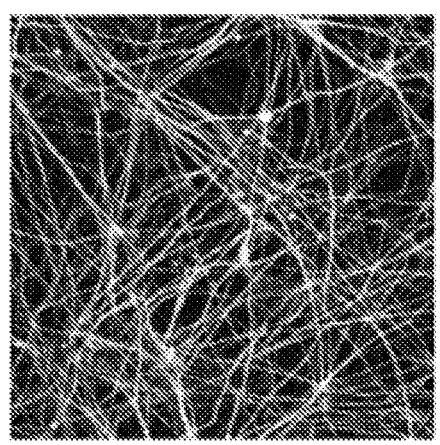

FIG. 8D shows a representative micrograph of 4 week-old hiPSC-derived hippocampal neuron cultures grown on a dPGA-laminin surface and stained with antibodies against Tubb3 (scale bar 50 um).

Figure 8E:
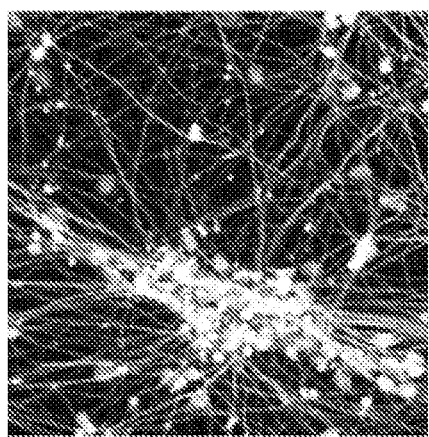

FIG. 8E shows a merged micrograph of FIGS. 8A and 8C.

Figure 8F:
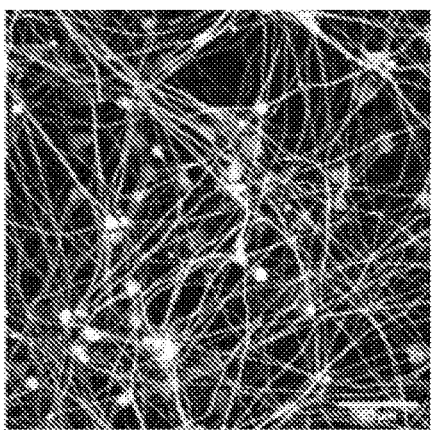

FIG. 8F shows a merged micrograph of FIGS. 8B and 8D.

Figure 8G:
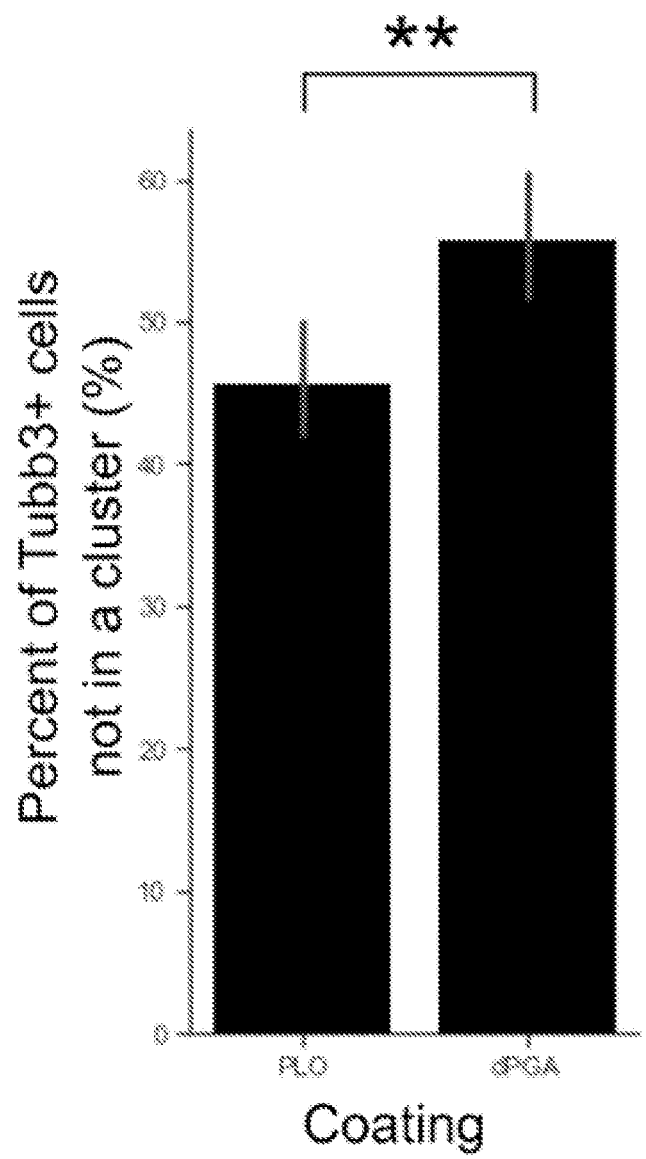

FIG. 8G is a graph showing the quantification of the percentage of Tubb3+ cells not found in clusters with other Tubb3+ cells (a cluster is defined as 2 or more cells located less than 1 μm apart) in 4 weeks-old hiPSC-derived hippocampal neuron cultures grown on a PLO-laminin or a dPGA-laminin (** $p<0.01$, paired two-tails Student's t-test n=16 and 20 respectively).

Figure 8H:
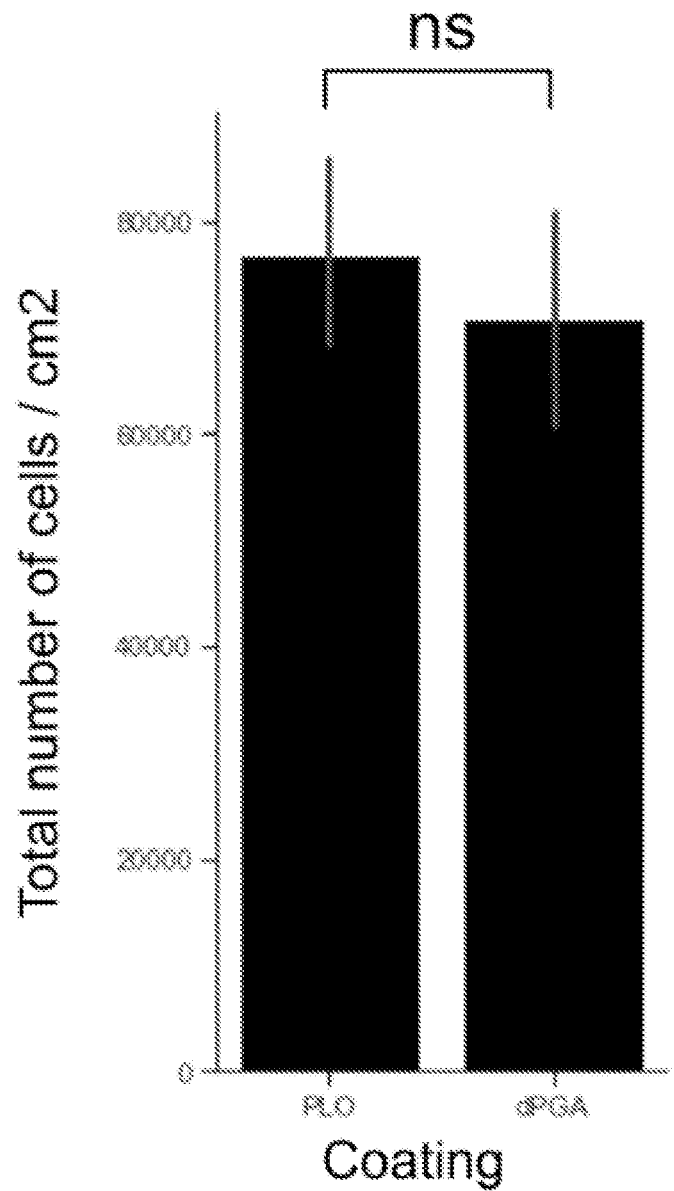

FIG. 8H is a graph showing the quantification of the total number cells in 4 weeks-old hiPSC-derived hippocampal neuron cultures grown on a PLO-laminin or a DPGA-laminin (ns $p>0.05$, paired two-tails Student's t-test n=16 and 20 respectively).

Figure 8I:
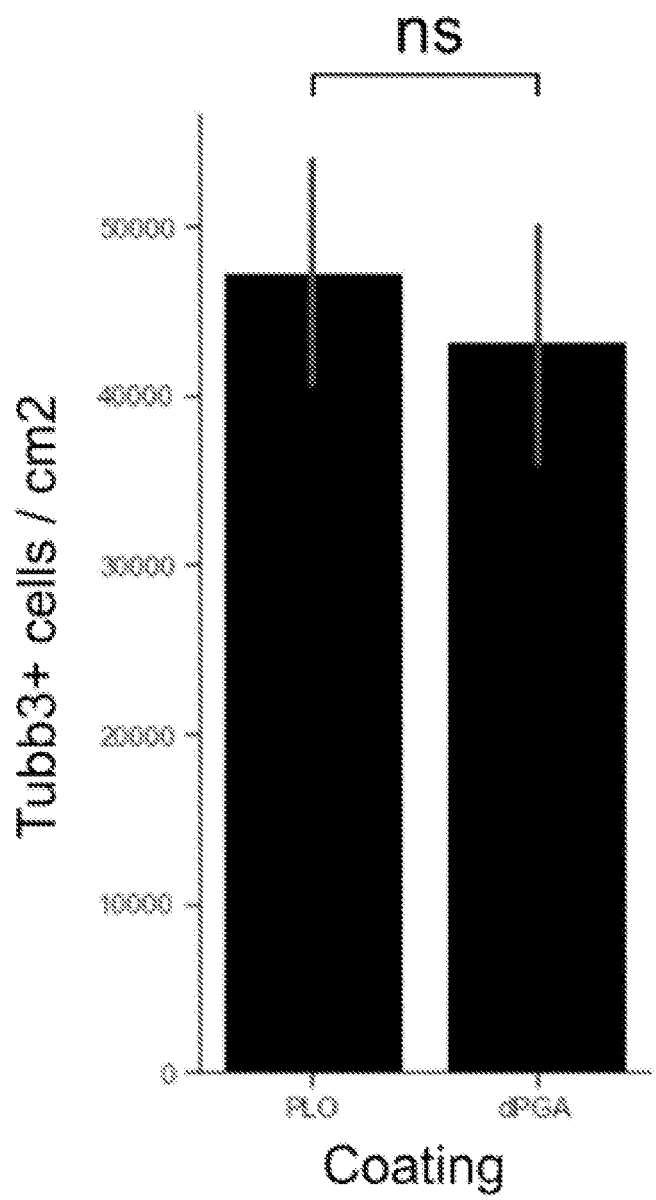

FIG. 8I is a graph showing the quantification of the Tubb3+ cells in 4 weeks-old hiPSC-derived hippocampal neuron cultures grown on a PLO-laminin or a DPGA-laminin (ns $p>0.05$, paired two-tails Student's t-test n=16 and 20 respectively).

Figure 8J:
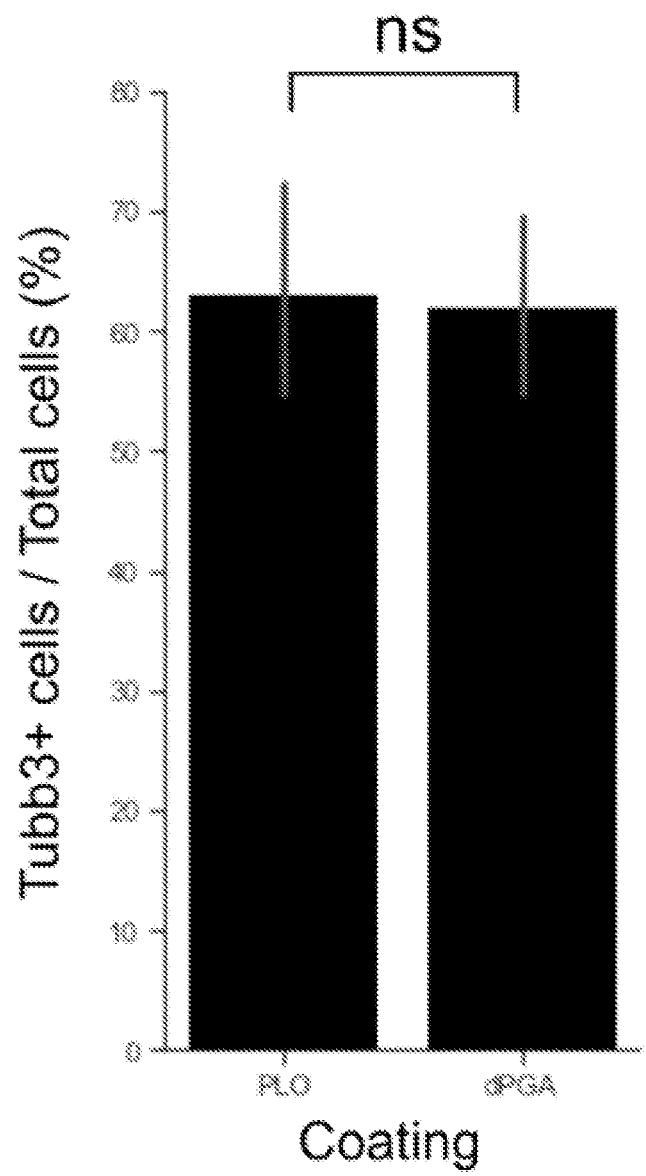

FIG. 8J is a graph showing the quantification of the percentage of Tubb3+ neurons to the total number of cells in 4 weeks-old hiPSC-derived hippocampal neuron cultures grown on a PLO-laminin or a DPGA-laminin (ns $p>0.05$, paired two-tails Student's t-test n=16 and 20 respectively).

Figure 9A:
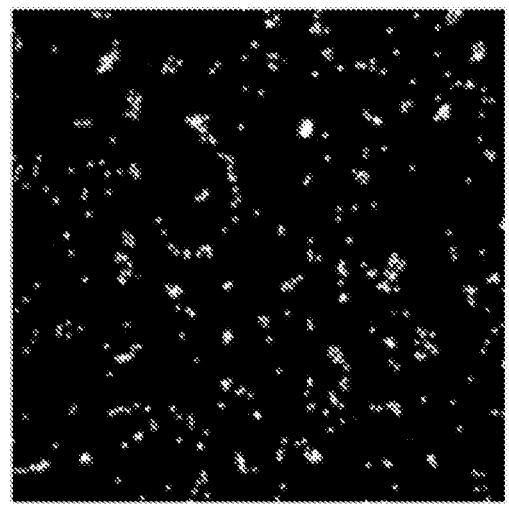

FIG. 9A shows a representative photomicrograph of 7 DIV primary rat cortical neurons grown on variations of the dendritic polyglycerol coating linked to dPGA and stained with nuclear marker Hoechst. (Scale bar is 100 μm).

Figure 9B:
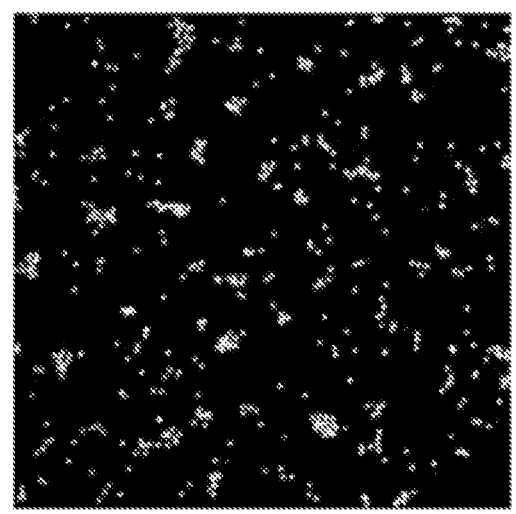

FIG. 9B shows a representative photomicrograph of 7 DIV primary rat cortical neurons grown on variations of the dendritic polyglycerol coating linked to dPGA-RGD and stained with nuclear marker Hoechst. (Scale bar is 100 μm).

Figure 9C:
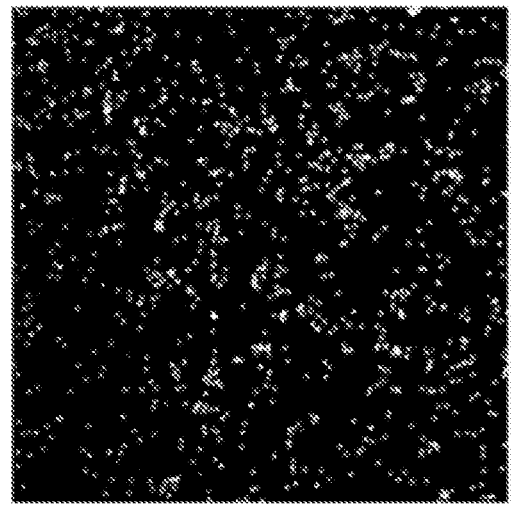

FIG. 9C shows a representative photomicrograph of 7 DIV primary rat cortical neurons grown on variations of the dendritic polyglycerol coating linked to dPGA-PDL and stained with nuclear marker Hoechst. (Scale bar is 100 μm).

Figure 9D:
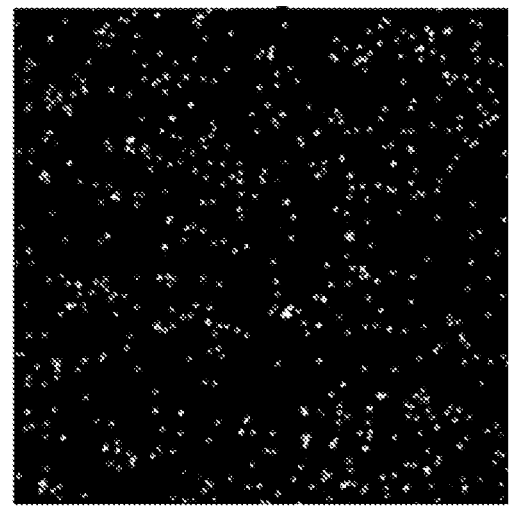

FIG. 9D shows a representative photomicrograph of 7 DIV primary rat cortical neurons grown on variations of the dendritic polyglycerol coating linked to dPGA-pAla and stained with nuclear marker Hoechst. (Scale bar is 100 μm).

Figure 9E:
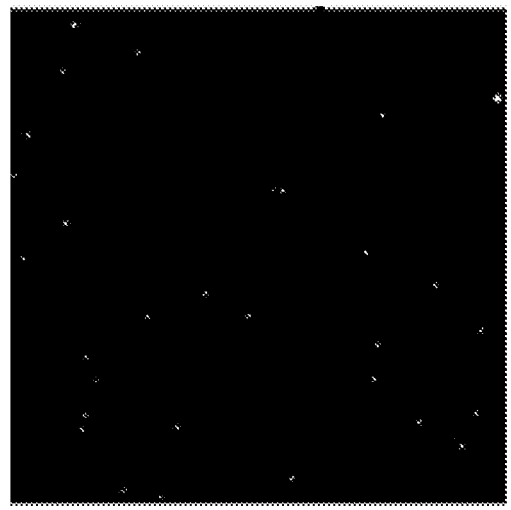

FIG. 9E shows a representative photomicrograph of 7 DIV primary rat cortical neurons grown on variations of the dendritic polyglycerol coating linked to dPGA-pGlu and stained with nuclear marker Hoechst. (Scale bar is 100 μm).

Figure 9F:
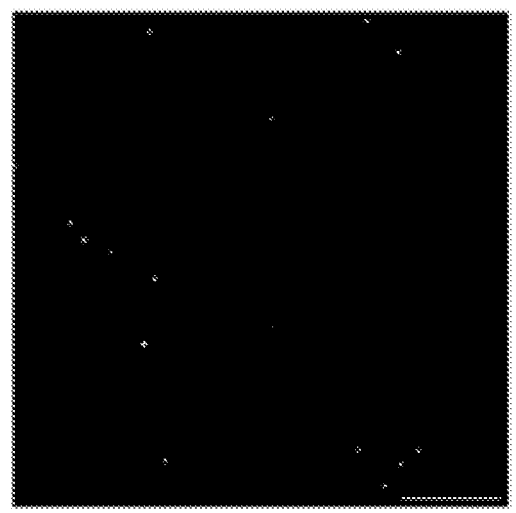

FIG. 9F shows a representative photomicrograph of uncoated 7 DIV primary rat cortical neurons and stained with nuclear marker Hoechst. (Scale bar is 100 μm).

Figure 9G:
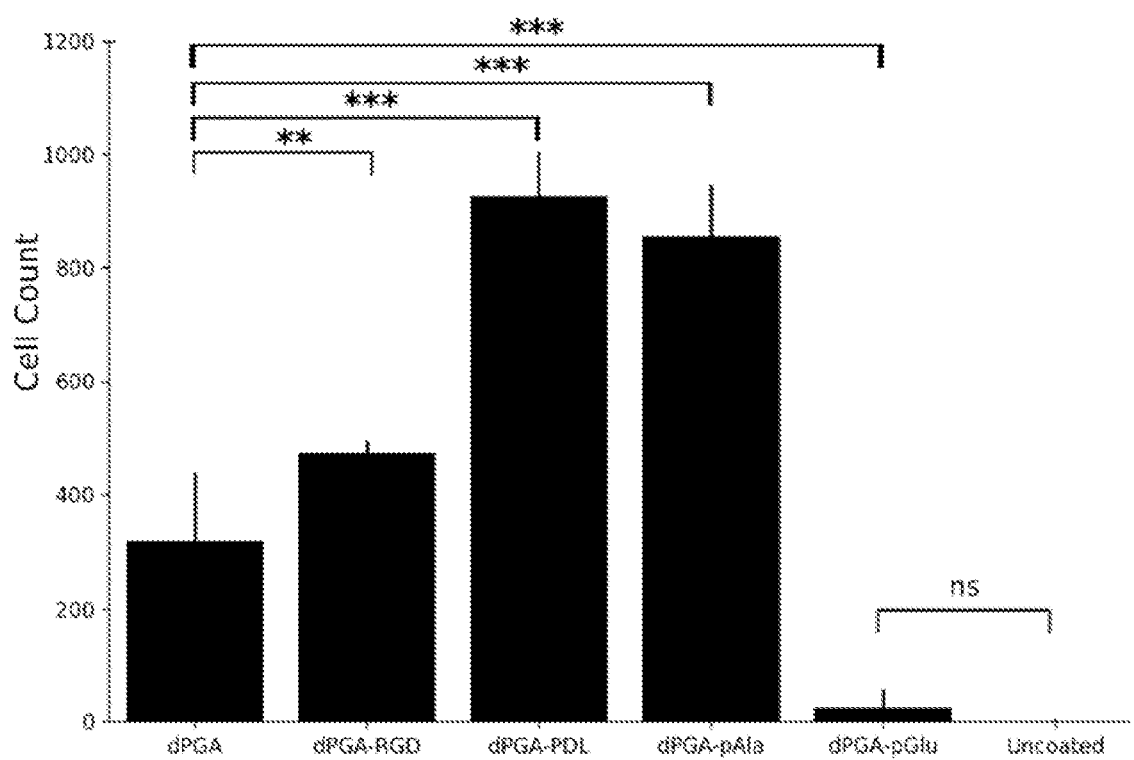

FIG. 9G is a graph showing the quantification of the number of cells present in 7 DIV primary rat cortical neurons grown on variations of the dendritic polyglycerol coating. (ns $p>0.05$, * $p<0.05$,  $p<0.01$, * $p<0.001$, one-way ANOVA with Bonferonni post-hoc test, n=6).

DETAILED DESCRIPTION

The present disclosure concerns a culture system for adherent cells or tissues which includes a plurality of cationic dendrimers on the surface of a solid support. The cationic dendrimer is a macromolecule biological mimetic of extracellular matrix components that promote cell adhesion, cell survival, cell division and/or cell differentiation. In some embodiments, the cationic dendrimer promotes the long-term stability of the cultured cells or tissues. Compared to existing solid support coatings, like poly-D-lysine, the cationic dendrimer described herein is resistant to proteolysis, easy to produce as well as being cost-efficient.

Culture System

The culture system of the present disclosure is intended to be used for the culture of adherent cells or adherent tissues. As it is known in the art, some cells and tissues require a physical association (e.g., via one or more cell membrane proteins for example) with a surface in order to be cultured and/or maintained in vitro. Such cells and tissues are referred to as adherent cells and adherent tissues. Failure of adherent cells or tissues to physically associate with a surface reduces their viability and may lead to cellular death (via necrosis or apoptosis). In the context of the present disclosure, adherent cells and adherent tissues cannot be cultured as suspended cells or suspended tissues (e.g., entities capable of remaining viable when cultured in the absence of a solid support in a suspension culture medium).

The present disclosure concerns the use of a cationic dendrimer to cover, at least in part, the surface of solid support for the culture of adherent cells or adherent tissues. In some embodiments, at least 5, 10, 15, 20, 25, 30, 35, 40, 45, 50, 55, 60, 65, 70, 75, 80, 85, 90, 91, 92, 93, 94, 95, 96, 97, 98, 99% or more of the surface of the solid support (intended to be in contact with the cultured cells or the cultured tissue) is associated (directly and/or indirectly) with the plurality of cationic dendrimers. In some embodiments, the entire surface of the solid support (intended to be in contact with the cultured cells or the cultured tissue) is associated (directly and/or indirectly) with the plurality of the cationic dendrimers.

The solid support provides a surface that can be composed of any material that is suitable for cell or tissue culture. In the context of the present disclosure, it is understood that the material of the surface solid support which is intended to be in contact with the cultured cell or tissue, in the absence of the cationic dendrimer, substantially lacks the ability to allow the cultured cells or tissues to adhere or maintain their viability. In some embodiments, the solid support is made from a material that can be sterilized or that is provided as being sterile. Known materials that can be present in the solid support include, but are not limited to, glass, plastic (such as, for example, polystyrene) as well as combinations thereof.

The solid support of the present culture system is provided in a format which is suitable for the culture of adherent cells and adherent tissues. The solid support provides a two-dimensional surface for cell or tissue cultures. It is however understood that the cationic dendrimer provided as well as the cultured cells or tissues can form a tridimensional organization on the surface of the solid support. In some embodiments, the solid support of the culture system can be provided as a substantially planar support. This includes, for example, cell or tissue culture flasks as well as cell or tissue culture plates (e.g., multiwall plates such as 6, 12, 24, 48, 96, 364 wells plate for example). The solid support of the culture system cannot be provided as a substantially spherical support (e.g., beads for example) since spherical supports, especially those having a diameter equal to or less than about 10 µM, do not allow the culture of adherent cells or tissues. In some embodiments, the solid support of the culture system cannot be provided in the form of a material for encapsulating the cultured cells or tissues.

The culture system comprises a plurality of cationic dendrimers. As it is known in the art, a "dendrimer" is a highly branched polymeric organic molecule with a three-dimensional architecture which may also be referred to as dendritic polymers, dendrons, arborols or cascade molecules. Dendrimers may or may not be symmetric about the core and in some embodiments, the dendrimers may adopt a spherical three-dimensional morphology. The dendrimers present in the culture system of the present disclosure bear a positive charge when placed at a physiological pH and are thus considered "cationic". The cationic dendrimers present in the culture system thus have the ability to be protonated at physiological pH (which can range between about 4.8 and 8.0 and is typically between 7.35 to 7.45). The cationic dendrimers, once associated (directly and/or indirectly) with the surface of the solid support, are considered non-toxic with respect to the adherent cells or tissues. In some embodiments, the cationic dendrimers can be sterilized and still maintain their ability to favor the adherence of cells or tissues and the stability of the cultured cells or tissues.

As shown in the Example section below, cationic dendrimers bearing functional amine groups allowed the adherence, the culture, the stability as well as the differentiation of adherent cells (e.g., neurons as well as neuronal progenitors). As such, the cationic dendrimers present in the culture system of the present disclosure comprise at least one, and in some embodiments, a plurality of functional amine groups to promote and maintain the culture of cells and tissues. In embodiments, the cationic dendrimers present in the culture system of the present disclosure include a single or a plurality of different types of cationic polymers.

In some embodiments, the cationic dendrimers of the present disclosure comprises free ends which can bear a functional group. The functional group can be used to facilitate the association of the cationic dendrimer to the cell or tissue, to improve the association of the cationic dendrimer to the surface of the culture support or both. In some embodiment, a functional amine group is included in the cationic dendrimer to facilitate the association with the cell or tissue. In some embodiments, the functional amine groups of the cationic dendrimer are located at the free ends of the polymers (thereby allowing their protonation at physiological pH). In some embodiments, the cationic dendrimers include at least about 25, 30, 35, 40, 45, 50, 55, 60, 65, 65, 70, 75, 80, 85, 90, 91, 92, 93, 94, 95, 96, 97, 98, 99% or more of the functional amine (when compared to the total functional groups that are present). In some embodiments, the cationic dendrimers include between about 25 to about 75% (and in some further embodiments, about 50%) functional amine groups (when compared to the total functional groups present in the cationic dendrimers). In some embodiments, the cationic dendrimers include 100% functional amine groups (when compared to the total functional groups present in the cationic dendrimers). In some embodiments, the cationic dendrimers include at some, but not all of its free ends, functional hydroxyl groups. In yet some additional embodiments, the cationic dendrimers include only functional amine and hydroxyl groups (and lack other types of functional groups).

The cationic dendrimer of the present disclosure can be made from any monomer that is suitable for cell/tissue culture. For example, the cationic dendrimer can be a poly(ethylenimine) (PEI) dendrimer made from a monomer of an amine group and two carbon aliphatic $CH_2$ $CH_2$ spacers. In another example, the cationic dendrimer can be a poly(amidoamine) (PAMAM) dendrimer made from a monomer comprising amide and amine. In yet another example, the cationic dendrimer can be a poly(glycerol) dendrimer made from a glycerol monomer. Glycerol is a monomer that is compatible with cell/tissue culture and can be used to make the cationic dendrimer of the present disclosure (e.g., a polyglycerol dendrimer). While polyglycerol dendrimers have been used for the delivery of cargo (such as nucleic acid molecules) to cells, prior to the filing of the present disclosure, it was not reported that polyglycerol dendrimers could be used to promote the adherence and the culture of cells or tissues. Suitable polyglycerol dendrimers include, but are not limited to, those described in WO2003033027 and WO2016166317, both incorporated herewith in their entirety.

In the culture system of the present disclosure, the cationic dendrimers are physically associated with the surface of the solid support. The physical association between the cationic dendrimers and the surface of the solid support should be strong enough so as to substantially limit the detachment of the cationic dendrimers when the culture system receives the cells or the tissues to be cultured as well as the culture medium. The physical association between the surface of the solid support and the cationic polymer can be electrostatic, ionic and/or covalent. In an embodiment, at least some of the cationic dendrimers have been adhered (directly and/or indirectly) to the surface of the solid support. In another embodiment, at least some of the cationic dendrimers have been covalently associated (directly and/or indirectly) with the surface of the solid support.

Each cationic dendrimer can be associated to the surface of the solid support at one or more discrete locations. In some embodiments, at least some (and in some further embodiments all) of the cationic dendrimer are directly associated with the surface of the solid support. In additional embodiments, at least some of the cationic dendrimers are indirectly associated with the surface of the solid support via another cationic dendrimer or another linking component of the solid support. In such embodiment, the indirectly associated cationic dendrimer is still considered associated to the surface of the solid support even though one or more linking elements (which may include a further cationic dendrimer) is present between the indirectly associated cationic dendrimer and the surface of the solid support.

In some specific embodiments, the cationic dendrimer can, prior to its association with the surface of the solid support, form aggregates with other cationic dendrimers and aggregates of the cationic dendrimers can associate (directly and/or indirectly) with the surface of the solid support. In some alternative embodiments, monodisperse cationic dendrimers can be associated (by adhesion or covalent association) with the surface of the solid support (directly or indirectly).

The culture system of the present disclosure can include further components such as, for example, synthetic polymers and/or components of the extracellular matrix. The further component, once incorporated in the culture system, must be suitable for cell or tissue culture. In some embodiments, the further component may be sterilized or be provided in a sterile form. In some embodiments, the further component is susceptible to proteolysis (which may occur by the metabolism of the cultured cells or tissues). The further component can be directly or indirectly associated with the surface of the solid support. In some embodiments, the solid support can include at least one further component that is directly associated to the surface of the solid support, at least one further component that is indirectly associated to the surface of the solid support or a combination thereof. Such further component can be used as a linking element between the cationic dendrimer and the surface of the solid support, can use the cationic dendrimer as a linking element to indirectly associate to the surface of the solid support and/or can be directly associated to the surface of the solid support without being associated to the cationic dendrimer.

One example of a synthetic polymer can be used as a further component of the culture system can be, for example, a synthetic polypeptide comprising a single type or a plurality of different types of amino acids (which can include amino acids in the L- or D-isomeric form). Synthetic polypeptides that can be used included in the culture system include, but are not limited to poly-L-lysine, poly-D-lysine, poly-L-ornithine and poly-D-ornithine.

Additional examples of synthetic polymers that can be used as a further component of the culture system can be, but are not limited to, polyethylene glycol (PEG), conductive polymers (such as poly(3,4-ethylenedioxythiophene) (PEDOT) or poly(3,4-ethylenedioxythiophene) polystyrene sulfonate (PEDOT-PSS)), silicon elastomers (such as polydimethylsiloxane or PDMS) and poly-lactic acid/poly (L-lactide) polymers.

As indicated herein, the further component can be a component of an extracellular matrix. Components of the extracellular cellular matrix include proteins (which may be glycosylated), components derived from proteins, lipids as well as carbohydrates (which include polysaccharides such as proteoglycans). Components of the extracellular matrix can be obtained from an animal source or from the recombinant expression in a genetically modified host. In an embodiment, the component of the extracellular matrix comprises a protein or a component derived from the protein (such as a peptide, the RGD peptide for example). In additional embodiments, the components of the extracellular matrix can be structural (e.g., fibrous) components of the matrix which can be, without limitation, collagen, elastin, fibronectin, laminin, thrombospondin, vitronectin, fragments thereof as well as combinations thereof. In a further embodiment, the components of the extracellular matrix have the ability to bind to at least one receptor on the surface of the cultured cell or cultured tissue (such as, for example, an integrin). In a specific embodiment, the culture system comprises, as the extracellular matrix component, laminin or a fragment thereof. In another specific embodiment, the culture system comprises, as the extracellular matrix component, a combination of different components such as, for example, Matrigel™ or Geltrex™, e.g., solubilized basement membrane preparations extracted from the Engelbreth-Holm-Swarm (EHS) mouse sarcoma. The components of the extracellular components can be obtained from the culture of cells producing them or can be synthetically made. The adherent cells or tissues cultured on the culture system described herein can synthesize and deposit one or more components of the extracellular matrix (directly and/or indirectly on the surface of the solid support).

The culture system of the present disclosure was designed to allow the adherence of cells or tissues to a solid support and allow their culture. In the Example section, it was shown that the culture system was able to allow the culture as well as maintain the viability of neuronal cells, but it is understood that other adherent cells as well as adherent tissues can be used with the culture system. The culture system of the present disclosure can be used for the culture of adherent cells and, in further embodiments, the culture system can comprise adherent cells. The culture system of the present disclosure is particularly advantageous for the culture of cells that typically cannot be cultured for more than three days or that exhibit a substantial reduction in viability when cultured for more than three days on a laminin or poly-L-lysine coating, such as, for example, neuronal cells or cells that be differentiated into neuronal cells.

In an embodiment, the adherent cells comprise primary cells (alone or in combination with other cell types). As it is known in the art, primary cells are directly harvested from a tissue or bodily fluid of a subject (which can be a human or an animal subject) and then submitted to in vitro cell culture. The cells can be obtained from any eukaryotic source, including, but not limited to mammals, such as humans and rodents (mouse or rat for example), non-mammal animals, plants, insects, etc. The primary cells can be primary embryonic cells, such as, for example primary embryonic neurons (including, but not limited to, cortical neurons and hippocampal neurons). In a specific embodiment, the primary cells are cortical neurons. The primary cells can be oligodendrocytes, astrocytes, microglial cells, peripheral blood mononuclear cells, fibroblasts, myocytes, endothelial cells, epithelial cells, etc.

In another embodiment, the adherent cells comprise stems cells (alone or in combination with other cell types). In such embodiment, the adherent cells can also comprise, cells which were differentiated, at least in part, from the stem cells. Stem cells refer to undifferentiated cells that can turn into any differentiated cell. Stem cells include, without limitation, embryonic stem cells, adult stem cells as well as induced pluripotent stem cells.

Partially differentiated cells obtained from the partial differentiation of stem cells, also referred to as progenitor cells, can also be used with or present in the culture system (alone or in the presence of stem cells and/or fully differentiated cells) as adherent cells. Progenitor cells include, but are not limited to, neural progenitor cells, hematopoietic progenitor cells and mesenchymal progenitor cells.

Fully differentiated cells obtained from the differentiation of stem cells or progenitor cells can also be used with or present in the culture system (alone or in the presence of stem cells and/or progenitor cells) as adherent cells. Such fully differentiated cells include, but are not limited to neurons (motor neurons, cortical neurons, dopaminergic neurons and/or hippocampal neurons), astrocytes, oligodendrocytes and myocytes.

In another embodiment, the adherent cells comprise immortalized cell lines which can be obtained from cancer isolates or be modified to become immortalized. Cells lines can be provided from any sources. Exemplary cell lines that can be included in the culture system include, without limitation, HEK 293 cells, CHO cells, PC12 cells, SH-SY5Y cells, HeLa cells and Caco2 cells. In an embodiment, the immortalized cell line comprises HEK 293 cells. In still another embodiment, the immortalized cell line comprises CHO cells.

Methods for Cell or Tissue Culture

The present disclosure also provides in vitro for the culture and optionally the maintenance of adherent cells or adherent tissues. The method thus comprise a step of contacting the adherent cells or tissues, the solid support as well as a culture medium for a period of time. The adherent cells or tissues can be maintained for a period of time of at least 3 consecutive days and remain substantially viable, exhibit an appropriate morphology and attached to the culture system. As it is known in the art, the expression "substantially viable" and "appropriate morphology" will differ between cell and tissue types. For example, when the adherent cells or tissues comprise primary neuronal cells, they are considered "substantially viable" when more than 15% of the original seeded cells remain alive during culture and exhibit the appropriate morphology (e.g., neurite growth by 24 h and large branching network by 7 days in culture). In another example, when the adherent cells or tissues comprise a cultured cell line, they are considered "substantially viable" when at least 50% of the seeded cells remain alive during culture. In some embodiments, the adherent cells or the cells of the adherent tissues are capable of proliferating (at least once or more) during the time period they are cultured in the culture system. The time period in which the cells or tissues are maintained in the culture system can be at least 3, 4, 5, 6, 7, 8, 9, 10, 15, 20, 25, 30, 35, 40, 45, 50, 55, 60, 65, 70, 75, 80, 85, 90 days or more. It is understood that during that time period, the culture medium can be changed once or more to provide the required nutrients to the cultured cells or tissues. Once the cells or tissues have been cultured for the desired period of time, the method can include detaching the cultured cells or tissues from the surface of the solid support (either through physical means or by enzymatic treatment). If necessary, the resulting cells or tissues can be stored prior to being used.

The method of the present disclosure also provides a way to differentiate stem cells into differentiated cells (e.g., progenitors cells or fully differentiated cells). In order to do so, such method comprises a step of contacting the adherent stem cells, the solid support as well as a culture medium for a period of time. At one point in time, a differentiating agent or cocktail is placed in the culture medium (which can be a fresh culture medium). As used in the context of the present disclosure, a differentiating agent or cocktail refers to one or more chemical and/or biological entity capable of causing the differentiation (partial or complete) of some or all cultured cells. The addition of the differentiating agent or cocktail can be made at the start of the cell culture or after the cells have been cultured for 1 or more days. The differentiating agent or cocktail does not need to be present the entire period the cells are being cultured in the culture system. The adherent stem cells (and cells derived from the differentiation thereof) can be maintained for a period of time of at least 3 consecutive days and remain substantially viable and attached to the culture system. In some embodiments, the adherent stem cells are capable of proliferating (at least once or more) during the time period they are cultured in the culture system. The time period in which the stem cells are maintained in the culture system (at least in part in the presence of the differentiating agent or cocktail) can be at least 3, 4, 5, 6, 7, 8, 9, 10, 15, 20, 25, 30, 35, 40, 45, 50, 55, 60, 65, 70, 75, 80, 85, 90 days or more. In some embodiments, in the culture system of the present disclosure, the adherent stem cells have a limited ability to clump, form cellular aggregates during culture and/or detach from the support. It is understood that during that time period, the culture medium can be changed once or more to provide the required nutrients to the cultured stem cells, differentiating cells, differentiated cells or combinations thereof. It is also understood that a different culture medium can be used to favor the viability or maintenance of the differentiating and/or differentiated cells. Once the differentiating and/or differentiated cells or tissues have been cultured for the desired period of time, the method can include detaching the cultured cells from the surface of the solid support (either through physical means or by enzymatic treatment). Once the cells have been cultured for the desired period of time, the method can include detaching the cultured cells from the surface of the solid support (either through physical means or by enzymatic treatment). If necessary, the resulting cells can be stored prior to being used.

In some specific embodiments, the methods of the present disclosure can be used to differentiate stem cells and limiting, in some embodiments avoiding, differentiating the stem cells into glial cells.

In an embodiment, the adherent cells submitted to the methods described herein comprises primary cells (alone or in combination with other cell types). The primary cells can be obtained from any eukaryotic source, including, but not limited to mammals, such as humans and rodents (mouse or rat for example), non-mammal animals, plants, insects, etc. The primary cells can be primary embryonic cells, such as, for example primary embryonic neurons (including, but not limited to, cortical neurons and hippocampal neurons). In a specific embodiment, the primary cells are cortical neurons.

The primary cells can be oligodendrocytes, astrocytes, microglial cells, peripheral blood mononuclear cells, fibroblasts, myocytes, endothelial cells, epithelial cells, etc.

In another embodiment, the adherent cells comprise stems cells (alone or in combination with other cell types). In such embodiment, the adherent cells can also comprise, cells which were differentiated, at least in part, from the stem cells. Stem cells refer to undifferentiated cells that can turn into any differentiated cell. Stem cells include, without limitation, embryonic stem cells, adult stem cells as well as induced pluripotent stem cells.

Partially differentiated cells obtained from the partial differentiation of stem cells, also referred to as progenitor cells, can also be used (alone or in the presence of stem cells and/or fully differentiated cells) in the methods described herewith. Progenitor cells include, but are not limited to, neural progenitor cells, hematopoietic progenitor cells and mesenchymal progenitor cells.

Fully differentiated cells obtained from the differentiation of stem cells or progenitor cells can also be used in the methods described herein (alone or in the presence of stem cells and/or progenitor cells). Such fully differentiated cells include, but are not limited to neurons (motor neurons, cortical neurons, dopaminergic neurons and/or hippocampal neurons), astrocytes, oligodendrocytes and myocytes.

In another embodiment, the adherent cells submitted to the present methods comprise immortalized cell lines which can be obtained from cancer isolates or be modified to become immortalized. Cells lines can be provided from any sources. Exemplary cell lines that can be included in the culture system include, without limitation, HEK 293 cells, CHO cells, PC12 cells, SH-SY5Y cells, HeLa cells and Caco2 cells. In an embodiment, the immortalized cell line comprises HEK 293 cells. In still another embodiment, the immortalized cell line comprises CHO cells.

In some embodiments, the cells that have been cultured according to the methods of the present disclosure can be introduced into another culture system, further analyzed in vitro, stored, etc.

In some embodiments, the cells that have been cultured according to the methods of the present disclosure can be introduced into a subject which may be the same subject which provided the adherent cells to be cultured or may be a different subject. The cultured cells can be differentiated fully or in part prior to the introduction into the subject.

Processes for Making the Culture System

The present disclosure further comprises processes for making the culture system described herewith. The process broadly comprises contacting a solution or a suspension comprising dissolved or suspended cationic dendrimers described herein with the surface of the solid support (intended to be used for cell or tissue culture). The contacting step should be made under conditions (temperature, time, pH, etc.) so as to allow the direct and/or indirect association between the surface of the solid support and the cationic dendrimers. The process can include, before, after and/or at the same time as the cationic dendrimers are being associated with the surface of the solid support, associating (directly and/or indirectly) a further component such as one or more synthetic polypeptide and/or one or more extracellular matrix components (laminin for example) to the surface of the solid support. The process can also include, in some embodiments, after the association between the surface of the solid support and the cationic dendrimers has been made, washing once or more the culture system (to provide a washed culture system), drying the culture system (to provide a dried culture system), sterilizing the culture system (to provide a sterile culture system) and/or storing the culture system (to provide a stored culture system).

The solution or suspension that is being placed into contact with the surface of the solid support can comprise, for example, at least 1, 2, 3, 4, 5, 6, 7, 8, 9, 10 μg or more of the cationic dendrimer per mL of the solution or the suspension.

The solution or suspension of the cationic dendrimer can be contacted with the surface of the solid support for at least 1, 2, 3, 4, 5, 6, 7, 8, 9, 10, 15, 20, 25, 30, 35, 40, 45, 50, 55, 60 minutes or more to allow the association. In some embodiments, the solution or the suspension of the cationic dendrimer can be contacted with the surface of the solid support overnight to allow the association.

The solution or suspension of the cationic dendrimers can be contacted with the surface of the solid support at a temperature between about 4 to about 70° C., and in some embodiments to a temperature of about 37° C. to cause the association. The person skilled in the art will realized that there is an interplay between the temperature and the incubation time of the solution or suspension of the cationic dendrimers to cause the association and that adjusting those conditions can be routinely done and optimized.

The solution or suspension of the cationic dendrimers, which can be provided in a sterile form, can include one or more salt, one or more buffering agent, etc. In some embodiments, the solution or suspension comprises a phosphate buffered saline. In some further embodiments, the methods can comprises a step of providing or making the solution or the suspension of the cationic dendrimers.

The present invention will be more readily understood by referring to the following examples which are given to illustrate the invention rather than to limit its scope.

Example I

Coating cell culture substrates. For experiments using dendritic polyglycerol amine (dPGA)-coated substrates, round 12 mm diameter Deutsche Spiegelglas borosilicate glass #1 coverslips (Carolina Biological Supply, Burlington, NC, USA) were sterilized and cleaned using a plasma cleaner (Plasma Harricks) for 1 min in normal atmosphere and then incubated overnight in the wells of a 24-well polystyrene cell culture plate (Corning) in 500 μl of a sterile solution of 1, 10, or 100 μg/ml of 150-300 kDa poly-d-lysine (PDL) (Sigma Aldrich, catalogue number P1149) or dPGA. in PBS in a cell culture incubator at 37° C. with 5% $CO_2$. Coated coverslips were then washed 3× with PBS before neurons were seeded the same day. When a coating of laminin-1 was added to the cationic polymer coating, coverslips were incubated with a solution of 1 μg/ml of murine laminin-1 (isolated from Engelbreth-Holm-Swarm murine sarcoma basement membrane) for 1 h at 37° C. and then washed 3 times with sterile PBS.

Embryonic rat cortical neuron culture. The results obtained were conducted in a study in accordance with the guidelines of the Canadian Council for Animal Care and approved by the Montreal Neurological Institute Animal Care Committee. All animals were housed in group housing and provided ad libitum access to food and water. Cell cultures were prepared from cerebral cortices of E18 Sprague Dawley rats as described (Banker, 1998). Briefly, cortices from multiple embryos were pooled and dissociated cells were plated at a density of ~25,000 cells/cm² in Dulbecco's Modified Eagle Medium with 10% fetal bovine serum and 1% Pen-Strep for 2 h to allow for cell adhesion before switching to Neurobasal medium containing 1% B27, 2 mM glutamax and 0.5% $N_2$. All cultures were maintained for 7-90 days in vitro (DIV) at 37° C. in a humidified 5% $CO_2$ incubator. 50% of the media was changed every 7 days (all reagents for which a source is not listed were obtained from Thermo Fisher Scientific, CA).

Immunocytochemistry. For immunolabeling, cells were fixed in 4% paraformaldehyde (PFA) for 12 min at room temperature, with the exception of labeling for synaptic markers, in which case cells were fixed in 100% methanol for 8-10 min at −20° C. Cells were then blocked using 10% horse serum (HS), 3% bovine serum albumin (BSA) in PBS with 0.3% Triton X-100 (Sigma-Aldrich) for 90 min at it Cells were incubated overnight with primary antibodies in blocking solution (10% HS, 3% BSA and 0.3% Triton X-100 in PBS). The following antibodies and dilutions were used: rabbit anti-NFM 1:1000 (Millipore), mouse anti-S-100β (Sigma Aldrich), rabbit anti-tyrosine-hydroxylase 1:1000 (Chemicon), mouse anti-tubulin β3 1:500 (BioLegend), mouse anti-NeuN 1:500 (Chemicon), guinea-pig anti-Synaptophysin-1 1:1000 (Synaptic System), mouse anti-PSD-95 1:500 (Thermo Fisher). After washing 3×15 min in PBS, cells were incubated with appropriate secondary antibodies: donkey anti-rabbit IgG Alexa 488™ (Invitrogen), goat anti-guinea-pig IgG Alexa 555™ (Invitrogen), donkey anti-mouse IgG Alexa 674™ (Invitrogen). Nuclei were labeled with the dye Hoechst 33342 (Thermo Fisher). Following labeling, cells were washed 3×15 min in PBS and then mounted using ProLong Gold™ (Thermo Fisher).

Cells were imaged with a Leica SP8 confocal microscope (Leica Microsystems). Images were analyzed via custom scripts in imageJ (NIH). Briefly, Hoechst stained nuclei were segmented automatically and a mask generated to count the number of labeled nuclei surrounded by a cytoplasm positive for the specific marker. Statistical tests were performed using custom Python scripts.

Electrophysiological Analysis. Whole cell patch clamp recordings were made from embryonic rat cortical neurons (14 DIV) prepared as described above. Neurons were plated on polymer coated glass coverslips at a density of ~50,000 cells/$cm^2$ in BrainPhys medium (StemCell technologies)+ B27 supplements instead of Neurobasal. Individual coverslips transferred to an upright SliceScope 2000 (Scientifica), and perfused with ACSF containing 135 mM NaCl, 3.5 mM KCl, 1.2 mM $MgCl_2$, 2 mM $CaCl_2$, 10 mM HEPES, and 20 mM D-Glucose (pH: 7.4, 300 mOsm). Current clamp recordings were performed using pipettes filled with 120 mM K-gluconate, 20 mM KCl, 10 mM HEPES, 7 mM phosphocreatine di-Tris, 2 mM $MgCl_2$, 0.2 ethylene-glycol-bis(b-aminoethyl ether)-N,N,N',N'-tetraacetic acid (EGTA), 4 mM Na-ATP, 0.3 mM Na-GTP (pH: 7.2-7.26, 280-290 mOsm). Access resistance was monitored throughout the recording, and cells were held at resting membrane potential. Current-clamp recordings were sampled at 20 kHz and filtered at 10 kHz using pClamp (v10.4, Molecular Devices).

Human iPSCs—Differentiation of cortical neurons from iPSCs. hiPSCs were cultured in Matrigel™-coated T25 flasks, in mTeSR medium (StemCell Technologies) that was changed daily for 8 days. On the ninth day, mTeSR was substituted with DMEM/F12 supplemented with 1× Glutamax™, non-essentials amino acids, 15% KOSR (Thermo Fisher), 1× N2 and 1× B27 supplements (Life Technologies), 100 ng/ml FGF8 (StemCell Technologies), 1 μM dorsomorphin (Tocris) and 1 μM SB431542 (Stemgent) and cultured for 1 week. hiPSC colonies were lifted off, cultured in suspension for 5 days to form EBs. EBs then were dissociated with accutase (Sigma), plated on a Matrigel™-coated dish and fed with expansion media composed of DMEM/F12 supplemented with 1× N2 supplement, 1× B27 supplement (Life Technologies), 1% penicillin/streptomycin, and 20 nM FGF2 (Prepotech) and 10 nM EGF (Prepotech). Emerging rosettes were dissociated completely using accutase and plated on poly-ornithine (50 μg/ml)/laminin (1 μg/ml) or dendrimer/laminin-coated dishes (laminin product number and concentration). NPCs were expanded and fed every 2 days. NPCs were differentiated into neurons using Neurobasal, 1× Glutamax, 1× B27, 1× N2, 20 ng/ml BDNF (Prepotech), 20 ng/ml GDNF (Prepotech), 1 ng/ml Compound E (Calbiochem) and 1 ng/ml VPA (Sigma).

Human iPSCs—Differentiation of dopaminergic neurons from iPSCs. Dopaminergic neurons were differentiated from hiPSCs following a modified version of a previously described protocol (Kriks et al. 2011). Briefly, cells were cultured in Matrigel™ (Corning)-coated T25 flasks with mTeSR medium (StemCell Technologies) that was changed daily for 8 days. On the ninth day, the mTeSR medium was replaced with DMEM/F12 medium supplemented with 1× Glutamax, non-essentials amino acids, 1% KOSR (Thermo Fisher), 1× N2 and 1× B27 supplements (Life Technologies), 100 ng/ml FGF8 (StemCell Technologies), 100 ng/ml SHH (Prepotech), 10 μM dorsomorphin (Tocris), 10 μM SB431542 (Stemgent), 10 uM BME, and cultured for 1 week. Following 3 DIV, 2 μM purmorphamine (Sigma), 200 ng/ml noggin (Prepotech) and 3 μM CHIR99021 (Selleckchem) were added. Next, cells were cultured in DMEM/F12 supplemented with 1× Glutamax™, non-essentials amino acids, 1× N2 and 1× B27 supplements (Life Technologies), 100 ng/ml FGF8 (StemCell Technologies), 100 ng/ml SHH (Prepotech), 2 uM purmorphamine, 200 ng/ml noggin and 3 μM CHIR99021 for 1 week in suspension for 5 days to form EBs. EBs then were dissociated with accutase (Sigma), plated on a matrigel-coated dish and fed with expansion media composed of DMEM/F12 supplemented with 1× N2 supplement, 1× B27 supplement (Life Technologies), 1% penicillin/streptomycin, and 20 nM FGF2 and 10 nM EGF. The emerging rosettes were dissociated completely using accutase and plated on a poly-ornithine/laminin or dendrimer/laminin-coated dishes. NPCs were expanded and fed every 2 days. NPCs were differentiated into dopaminergic neurons using Neurobasal, 1× B27, 1× N2, 20 ng/ml BDNF, 20 ng/ml GDNF, 1 ng/ml compound E, 0.2 mM ascorbic acid (Sigma), 0.5 mM dbcAMP (Carbosynth) and 1 ng/ml TGF3β (Prepotech).

Figure 1A:
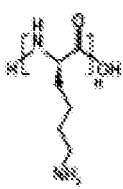
FIG. 1A is a representation of poly-d-lysine (PDL).
Figure 1B:
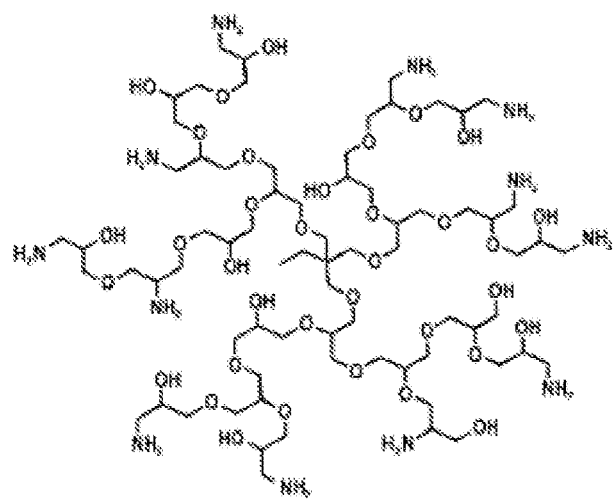
FIG. 1B is a representation of dendritic polyglycerol amine (dPGA) polymers. It will be appreciated that the structure of dPGA on this figure has been scaled down and simplified and is provided only for comparing it to the structure of PDL.

Human iPSCs—Differentiation of hippocampal neurons from iPSCs. iPSCs were derived from fibroblasts using a Cyto-Tune Sendai reprogramming kit (Invitrogen) according to the manufacturer's instructions. All iPSCs were characterized as previously described (Brennand et al., 2011). iPSC colonies were cultured on Matrigel-coated dishes (BD Biosciences) using mTeSR1 medium (StemCell Technologies). Embryoid bodies were formed by mechanical dissociation of iPSC colonies using collagenase and plating onto low-adherence dishes. For embryoid body differentiation, floating embryoid bodies were treated in STEMdiff™ Neural Induction Medium+SMADi (StemCell Technologies) for 20 days. To obtain neural progenitor cells, embryoid bodies were then plated onto polyornithine/laminin (Sigma)-coated dishes in DMEM/F12 plus N2 and B27. Rosettes were manually collected and dissociated with accutase (Chemicon) after 1 week and plated onto dendrimer (50 μg/ml) and laminin-coated dishes in neural progenitor cell media (DMEM/F12, 1× N2, 1× B27 (Invitrogen), and 20 ng/ml EGF, and 20 ng/ml FGF2 (Invitrogen)). To obtain hippocampal mature neurons, neural progenitor cells were plated onto dendrimer and laminin coated-dishes and differentiated in BrainPhys neuronal medium (StemCell Technologies) supplemented with 1× N2, 1× B27, 20 ng/ml BDNF (Peprotech), 1 mM dibutyrl-cyclicAMP (Sigma), 200 nM ascorbic acid (Sigma), 1 μg/ml laminin and 620 ng/ml Wnt3a (R&D) for 2 weeks. After 2 weeks post differentiation, media was replaced by STEMdiff™ Forebrain Neuron Maturation Kit (StemCell Technologies) in BrainPhys media until use. All cells used in the present study were verified as free from mycoplasma contamination.

dPGA-substrate coating supports primary mammalian neuronal cells in culture. Substrates coated with poly-cationic peptides are widely employed to support the adherence and survival of neural cells in culture. Poly-lysine is the most commonly used polymer for primary neuronal culture, however peptide-based cell culture coatings are sensitive to proteolysis and are degraded by cells in vitro. It was therefore determined if a non-peptidergic poly-cationic polymer might provide enhanced support for long term cell culture. Primary neurons seeded on a cell culture surface coated with dPGA were compared to a standard poly-lysine coating. The comparison focused on the d enantiomer of poly-lysine, PDL, due to its relative resistance to trypsin-like proteases (compared to poly-L-lysine or ploy-L-ornithine coatings (FIGS. 1A and 1B).

A cell culture substrate, such as a clean glass coverslip, is typically coated with PDL by adsorption from a PDL solution in the range of 10-100 μg/ml. Here, plasma cleaned glass coverslips coated in parallel with concentrations of 1, 10 and 100 μg/ml of PDL or dPGA were compared, testing the typical range of concentration used as a coating solution. Although coating for 1 h is generally sufficient and previous studies have concluded that most of the polymer is adsorbed within the first 5-10 min, the culture surfaces were incubated overnight at 37° C. to preclude any difference in coating efficiency due to any possible differences in adsorption kinetics of the different polymers.

Figure 1C:
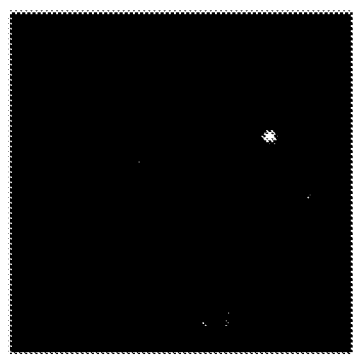
FIG. 1C is a representative photomicrograph of 7 days in vitro (DIV) primary rat cortical neurons grown in a concentration of 1 µg/mL) of PDL-coated glass coverslips labeled for nuclear stain Hoechst 33342 (scale bar is 30 µm).
Figure 1D:
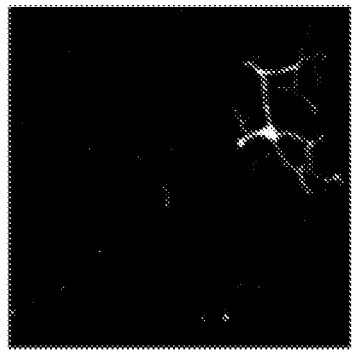
FIG. 1D is a representative photomicrograph of 7 days in vitro (DIV) primary rat cortical neurons grown in a concentration of 1 µg/mL) of PDL-coated glass coverslips labeled for neurofilament M (Nfm) (scale bar is 30 µm).
Figure 1E:
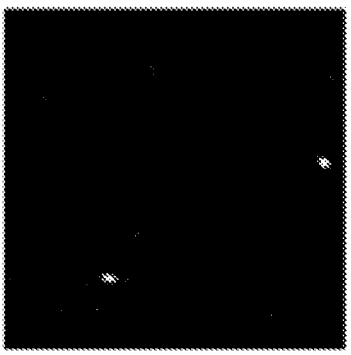
FIG. 1E is a representative photomicrograph of 7 days in vitro (DIV) primary rat cortical neurons grown in a concentration of 1 µg/mL) of either dPGA-coated glass coverslips labeled for nuclear stain Hoechst 33342 (scale bar is 30 µm).
Figure 1F:
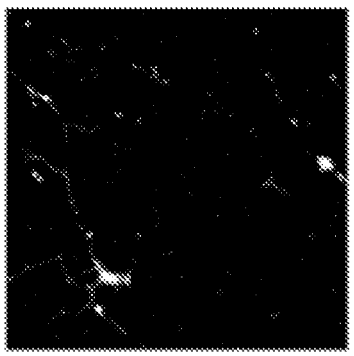
FIG. 1F is a representative photomicrograph of 7 days in vitro (DIV) primary rat cortical neurons grown in a concentration of 1 µg/mL) of dPGA-coated glass coverslips labeled for neurofilament M (Nfm) (scale bar is 30 µm).
Figure 1G:
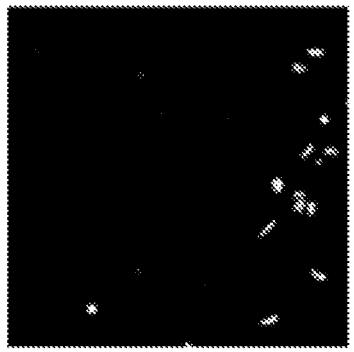
FIG. 1G is a representative photomicrograph of 7 days in vitro (DIV) primary rat cortical neurons grown in a concentration of 10 µg/mL) of PDL-coated glass coverslips labeled for nuclear stain Hoechst 33342 (scale bar is 30 µm).
Figure 1H:
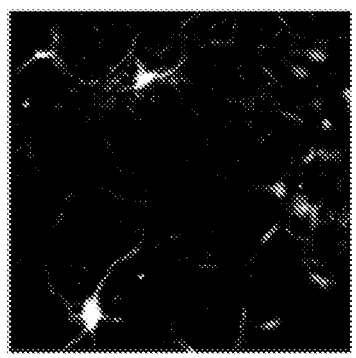
FIG. 1H is a representative photomicrograph of 7 days in vitro (DIV) primary rat cortical neurons grown in a concentration of 10 µg/mL) of PDL-coated glass coverslips labeled for neurofilament M (Nfm) (scale bar is 30 µm).
Figure 1I:
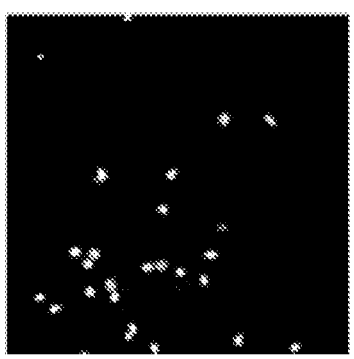
FIG. 1I is a representative photomicrograph of 7 days in vitro (DIV) primary rat cortical neurons grown in a concentration of 10 µg/mL) of either dPGA-coated glass coverslips labeled for nuclear stain Hoechst 33342 (scale bar is 30 µm).
Figure 1J:
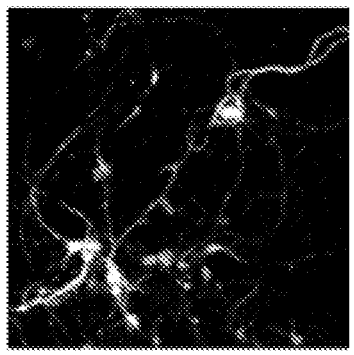
FIG. 1J is a representative photomicrograph of 7 days in vitro (DIV) primary rat cortical neurons grown in a concentration of 10 µg/mL) of dPGA-coated glass coverslips labeled for neurofilament M (Nfm) (scale bar is 30 µm).
Figure 1K:
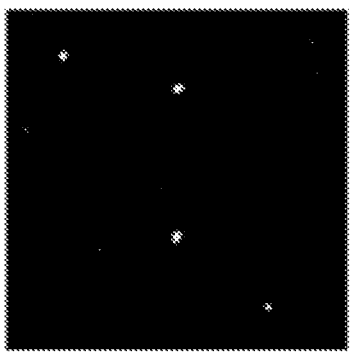
FIG. 1K is a representative photomicrograph of 7 days in vitro (DIV) primary rat cortical neurons grown in a concentration of 100 µg/mL) of PDL-coated glass coverslips labeled for nuclear stain Hoechst 33342 (scale bar is 30 µm).
Figure 1L:
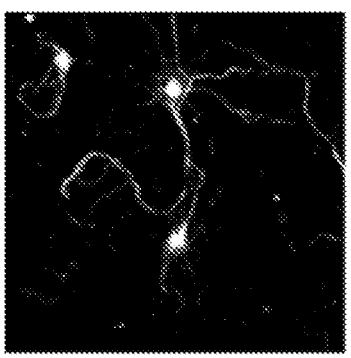
FIG. 1L is a representative photomicrograph of 7 days in vitro (DIV) primary rat cortical neurons grown in a concentration of 100 µg/mL) of PDL-coated glass coverslips labeled for neurofilament M (Nfm) (scale bar is 30 µm).
Figure 1M:
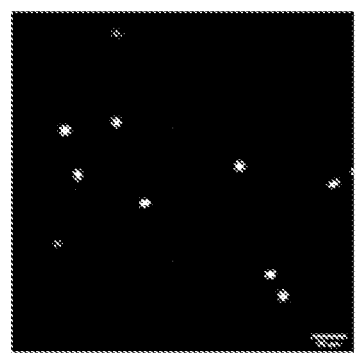
FIG. 1M is a representative photomicrograph of 7 days in vitro (DIV) primary rat cortical neurons grown in a concentration of 100 µg/mL) of either dPGA-coated glass coverslips labeled for nuclear stain Hoechst 33342 (scale bar is 30 µm).
Figure 1N:
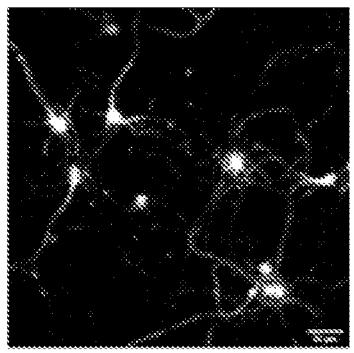
FIG. 1N is a representative photomicrograph of 7 days in vitro (DIV) primary rat cortical neurons grown in a concentration of 100 µg/mL) of dPGA-coated glass coverslips labeled for neurofilament M (Nfm) (scale bar is 30 µm).
Figure 1O:
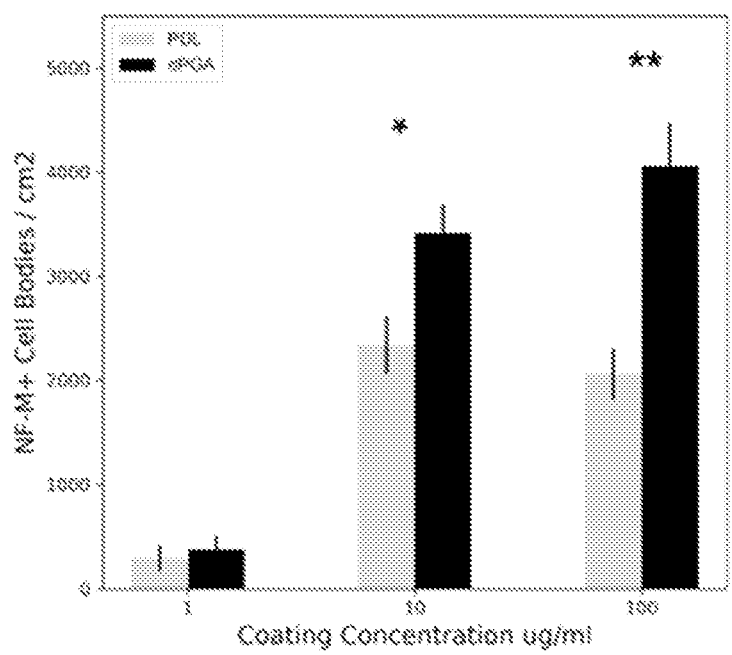
FIG. 1O is a graph showing the quantification of the number of NFm+ positive cells in 7 DIV primary rat cortical cultures grown on glass coverslips treated with increasing concentration (1, 10 or 100 µg/mL) of either PDL or dPGA (* $p<0.05$, ** $p<0.01$, paired two-tailed Student's t-test n=4).
Figure 1P:
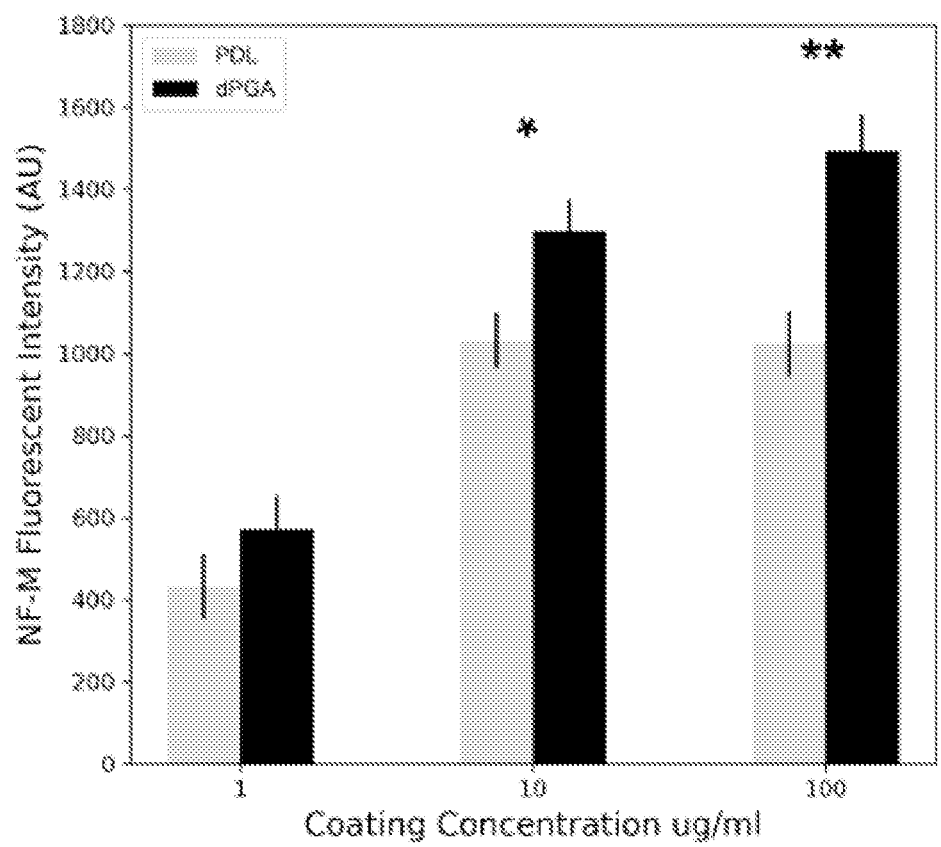
FIG. 1P is a graph showing the quantification of NFm fluorescent intensity of 7 DIV primary rat cortical cultures grown on glass coverslips treated with increasing concentration (1, 10 or 100 µg/mL) of either PDL or dPGA (* $p<0.05$, ** $p<0.01$, paired two-tailed Student's t-test n=4).

To evaluate whether dPGA coated surfaces could support the adhesion and survival of neuronal cells in vitro, the coated coverslips were seeded with dispersed primary neocortical neurons derived from embryonic day 18 (E18) rat cortices. It was found that 12 mm diameter round glass coverslips coated with 0.5 ml/coverslip of PDL or dPGA at 10 or 100 μg/ml in distilled $H_2O$ were sufficient for primary cortical neurons to adhere to the culture surface within 1 h after seeding and that both of these surfaces similarly supported neuronal survival and neurite extension for several days afterward (FIGS. 1C-1P).

Following 7 DIV, cultures were fixed and labeled using antibodies against the neuron-specific medium molecular weight neurofilament subunit (NFM), and the glial specific marker S100β. The number of cells positive for these markers was counted, providing an assessment of the basic characteristics of the cells in the cultures. It has been reported that certain polycationic surface coatings may impact the proliferation or differentiation of either neurons or glia (FIGS. 1C-1N). The results revealed an ~50% greater density of neurons grown on substrates coated with 10 μg/ml dPGA compared to PDL ($p<0.05$), and an ~96% higher neuronal density on substrates coated with 100 μg/ml coating of dPGA compared to PDL ($p<0.01$) (FIG. 1O).

Unlike the substrates coated with 10 or 100 μg/ml PDL or dPGA, coatings using 1 μg/ml of either polymer resulted in few surviving neurons, and the limited number of cells detected exhibited a stunted morphology with minimal neurite extension and extensive surface blebbing. These findings indicate that coating a glass substrate with a solution of 1 μg/ml of either PDL or dPGA, using the methodology detailed here, is insufficient to maintain healthy adherent cortical neurons in culture. Phase contrast imaging before fixation was sufficient to detect the sparse distribution of surviving neurons, indicating that the few cells present after immunolabeling are not due to cellular detachment during the fixation, washing and labeling protocol, but rather reflects the inability of cells to adhere and survive on a minimally coated glass surface. Few S100β positive glial cell bodies were present in these 7 DIV cultures, and the few cells detected did not appear to be significantly affected by the type of substrate used (data not shown).

dPGA supports primary cortical neurons in vitro for at least 3 months. PDL is more resistant to proteolysis by trypsin than PLL, but is susceptible to degradation by other proteases. In contrast, the poly-glycerol core of dPGA entirely lacks peptide bonds and is highly resistant to degradation by cellular proteases. It was therefore investigated whether a substrate coated with dPGA might support more stable longer-term cell cultures. To test this, cultures of E18 rat primary cortical neurons were grown on either a dPGA or PDL coated substrate for 90 DIV (3 months). In all conditions, fewer neurons were detected compared to 7 DIV, consistent with neuronal density typically decreasing over the first 2 months of culture. The neurons remaining appeared healthy with large cell bodies, extensive arborisations and synaptic connections (FIGS. 2A-2R). Quantification revealed that the number of neurons supported by the dPGA coated substrate was ~3-fold more compared to the PDL substrate ($p<0.001$) (FIGS. 2S and 2T). A substantial increase was detected in the density of glial cells at 3 months in vitro compared to 7 DIV. S100β positive cells with astrocyte-like morphology formed a largely confluent layer. Slightly more S100β positive cells were detected on the 10 μg/ml dPGA-coated substrate compared to 10 μg/ml PDL-coated substrate, but no difference in glial cell density was found when the substrates were coated with 100 μg/ml (FIGS. 3A-3F). Notably, the enhanced capacity of the dPGA substrate to support neurons was apparent only at 10 μg/ml. Fewer neurons were detected in cultures coated with 100 μg/ml dPGA compared to the 10 μg/ml dPGA coating, with neuronal and glial cell densities that were not significantly different from the cultures coated with 100 μg/ml of PDL.

Primary neocortical neurons differentiate, polarize, and elaborate synaptic connections on a dPGA coated substrate. The findings described above provide evidence that a dPGA coated substrate improves neuronal survival in culture, however it was not clear if this novel material may impact neuronal differentiation and function in vitro. We therefore tested for possible differences between neurons grown on PDL or dPGA. Cells were immunocytochemically labeled using the neuron-specific markers beta III Tubulin (tubb3), NFM, and the neuronal nuclear marker NeuN. Examining cells grown on dPGA or PDL coated substrates at 12 DIV we found similar neuronal polarization and process elaboration (FIGS. 4A-4H).

A hallmark of neuronal differentiation is the capacity to form synapses and propagate electrophysiological signals. Examining cultures grown on PDL or dPGA substrates following 12 DIV, the presynaptic marker synaptophysin-1 and glutamatergic postsynaptic marker PSD-95 were marked and their distribution along neurites was evaluated. Embryonic rat cortical neurons grown on substrates coated with 10 μg/ml of either dPGA or PDL exhibited similar immunoreactivity for synaptophysin-1 and PSD95 (FIGS. 4I-4P), with punctate enrichments distributed along neurites. Partially overlapping puncta of the two proteins were readily detected along adjacent neurites, consistent with pre- and post-synaptic specializations (FIGS. 4Q-4X). Although a dPGA coated substrate provides better support for neuronal survival in long term culture, as described above, in the neurons present no differences were readily apparent in the intensity or distribution of these synaptic markers along neurites between cultures grown on substrates coated with PDL compared to dPGA. These findings support the conclusion that dPGA is a superior substrate to PDL to support and maintain short and long-term cultures of primary cortical neurons, without significantly altering neuronal physiology. Electrophysiological patch-clamp recordings show that primary cortical neurons grown on glass coverslips coated with 10 µg/ml of dPGA are capable of generating electrophysiological activity and synaptic transmission in a manner indistinguishable from primary cortical neurons grown on a standard PDL-coated surface. The neurons produce action potentials following membrane depolarization with similar wave forms (FIGS. 5A and 5B) and amplitude (FIGS. 5D and 5F) as neurons grown on PDL-coated coverslips. They maintain a similar resting membrane potential (FIG. 5C) and the membrane resistance (FIG. 5E) is the same suggesting a similar balance of expressed ion channels.

Matching our synaptic marker data, voltage clamp recordings showed spontaneous inhibitory and excitatory synaptic potentials indicative of networks activity and of functional synaptic transmission within the network (FIGS. 5G-5R). When maintaining the membrane of the recorded neurons at −70 mV, we detected individual current outflow events (FIGS. 5G and 5H) indicative of excitatory post-synaptic currents from excitatory synaptic inputs with comparable amplitude (FIGS. 5I and 5J) and frequency (FIGS. 5K and 5L) in both culture conditions. Similarly, when maintaining the membrane of the recorded neurons at 0 mV, we detected individual current inflow events (FIGS. 5M and 5N) indicative of inhibitory post-synaptic currents from inhibitory synaptic inputs with comparable amplitude ((FIGS. 5O and 5P) and frequency (FIGS. 5Q and 5R) in both culture conditions. No statistically significant differences between neocortical neurons grown on our novel dPGA- or on PDL-coated surfaces were found in any of the electrophysiological properties that we investigated. These findings support the conclusion that dPGA is a superior substrate to PDL to support and maintain short and long-term cultures of primary cortical neurons, without significantly altering neuronal physiology.

dPGA substrate supports long-term human iPSC-derived cortical neuron cultures. The poly-cationic peptide poly-ornithine is also routinely used as a substrate coating for cell culture and, in particular, is often applied to support the differentiation and maintenance of iPSC-derived neuronal cells. A major application for human iPSC-derived neurons is to study age related neurodegenerative diseases, and these cells in particular, would benefit from protocols that enhance the stability of long-term cultures. It was therefore explored if replacing PLO with a dPGA cell culture substrate would enhance the stability of long-term cultures of human iPSC-derived neurons. A typical configuration to support iPSC derived neurons is a base layer of PLO followed by a layer of recombinant laminin, or a layer of Matrigel™ without a PLO base layer.

It was first tested whether dPGA could provide an economical alternative to replace substrate coatings of Laminin or Matrigel™, but human iPSC-derived cortical neurons did not survive on a substrate coated with dPGA alone (data not shown). Like PLO, dPGA presents a positively charged electrostatic surface, but does not contain the specific receptor binding sties present in a protein like laminin-1. It was then tested whether dPGA might replace and enhance the foundation layer of PLO used under the laminin layer.

Human neural progenitor cells were plated during the final differentiation step for cortical neurons onto substrates coated with 50 µg/ml of dPGA-laminin or 50 µg/ml of PLO-laminin. Following 1 week in culture, inspection with phase contrast microscopy revealed that the cultures maintained on substrates of dPGA-laminin were healthier and more exuberant than cultures grown on PLO-Laminin. A higher density of neurons was apparent, with more extensive arborisations, less cell body aggregation, and fewer undifferentiated cells with stem-cell-like morphology. Following 2 weeks, the hiPSC-derived cultures were immunolabeled for NFM and S100β, and stained with Hoechst dye. Quantification detected ~10% more iPSC-derived cortical neurons on the dPGA-laminin coated substrate compared to cultures grown on the standard PLO-laminin substrate (FIGS. 6A-H). Total cell density, determined by counting Hoechst labelled nuclei, was lower in dPGA-laminin compared to PLO-laminin cultures. Immunostaining and quantification reveled that PLO-laminin cultures contained approximately twice as many S100β positive glial cells as the dPGA-laminin cultures (FIGS. 6I-6K). The reduced numbers of glial cells combined with higher numbers of neurons resulted in a higher ratio of cortical neurons when cultured on dPGA-laminin, and suggests a bias toward neuronal differentiation in the cultures maintained on the dPGA-laminin substrate (FIGS. 6I-6K). The spatial distribution of cells within the cultures was also different, with NFM-negative cells on PLO-laminin substrates tending to form large dense aggregate clusters, likely of dividing cells, while the cells growing on dPGA-laminin were more evenly distributed.

dPGA supports human iPSC derived dopaminergic neurons. The results described above provide evidence that a layer of dPGA is a superior cell culture substrate compared to a number of standard coatings for primary or iPSC-derived cortical neurons. To test its generalizability and potentially extend the utility of dPGA as a cell culture substrate, we then tested its capacity to support human iPSC derived dopaminergic neurons and hippocampal neurons. These neurons are of notable interest because of their potential to model human age related neurodegenerative disease when derived from patient suffering from Parkinson's disease and Alzheimer's disease.

Following the final differentiation step toward midbrain dopaminergic neurons, the neural progenitor cells were seeded using the same conditions as described above for iPSC-derived cortical neurons. Glass coverslips were coated with a solution of either 50 µg/ml dPGA or PLO followed by a 2 h incubation with a solution of 1 µg/ml recombinant laminin. After 14 DIV the cultures were immunolabeled for the dopaminergic neuronal marker tyrosine hydroxylase (TH) and general neuronal marker beta III Tubulin, and with Hoechst dye to label nuclei (FIGS. 7A-7H). In these cultures, it is important to identify the dopaminergic neurons as current protocols for the generation of midbrain dopaminergic neurons from hiPSC yield a mixture of dopaminergic and non-dopaminergic neurons. Quantification of the different cell types indicated that the dPGA-laminin substrate resulted in significantly more TH-positive neurons compared to cultures grown on the PLO-Laminin substrate. Surprisingly, although more TH-positive neurons were detected, the dPGA-laminin condition also resulted in fewer total tuj1-positive neurons and fewer total cells overall (Hoechst positive nuclei) compared to the PLO-laminin substrate. These findings support the conclusion that the dPGA-laminin substrate better supports differentiation toward the targeted dopaminergic neuronal cell type (FIGS. 7I-7K).

As for hiPSC-derived hippocampal neurons, following the final differentiation step toward hippocampal fate, the neural progenitor cells were similarly plated on glass coverslips coated with a solution of 50 µgml of either dPGA or PLO followed by a second coating with 1 µm/ml solution of laminin. After 28 days in culture, the cells were immunolabeled with the neuronal marker beta III Tubulin and nuclear dye Hoechst (FIGS. 8A-8F). In contrast to the results obtained by plating neocortical and dopaminergic neurons on dPGA coated surfaces, no significant difference in the total number of cells, the total number of beta III Tubulin positive neurons or the percentage of cells differentiated into hippocampal neurons over the total number of cells was observed (FIGS. 8H-J) in hiPSC-derived hippocampal neurons grown on dPGA coated surface compared to neurons plated on standard PLO-coated surface. However, a slight tendency was noticed for hiPSC-derived hippocampal neurons to aggregate into clusters, rather than be evenly distributed in culture grown on PLO-coated glass compared to cultures grown on dPGA-coated glass. Quantification of the number of beta III Tubulin positive cells found within a cluster (defined as 2 or more beta III Tubulin positive neurons located less than 1 µm apart) showed that a larger proportion of hippocampal neurons were found in clusters in cultures that were seeded on PLO-coated surfaces compared to cultures seeded on dPGA-coated glass (FIG. 8G). These findings suggest that the dPGA-laminin substrate supports, but does not improve the survival or differentiation of hiPSC-derived hippocampal neurons. However, a dPGA-laminin substrate does seem to reduce cell aggregation of hiPSC-derived hippocampal neurons following 28 DIV, thus promoting a more even distribution of the neurons in culture.

Example II

Additional cells have been cultured using the dPGA-coated substrate described in Example I. The tables below provides the number of days in which these cells have been cultured as well as the phenotype observed using different coatings.

TABLE 1

Additional cells cultured with the dPGA-coated substrate.

| Type of cell | Culture conditions | Species | Number of days in vitro |
| --- | --- | --- | --- |
| Cortical neurons | Primary cells | Rat | 90 |
| Oligodendrocytes | Primary cells | Rat | 21 |
| Astrocytes | Primary cells | Rat | 7 |
| Microglia | Primary cells | Rat | 7 |
| Motor neuron | iPSC-derived cells | Human | 60 |
| Cortical neuron | iPSC-derived cells | Human | 60 |
| Hippocampal neuron | iPSC-derived cells | Human | 30 |
| Dopaminergic neuron | iPSC-derived cells | Human | 60 |
| HEK 293 | Immortalized cell line | Human | 7 |

TABLE 2

Phenotypes observed in cultures grown on dPGA-coated surface compared to a standard coating (Y = yes, N = no).

| Cell Type | Standard Coating | Increased cell survival | Increased differentiation | Reduced cell aggregation | Increased culture lifespan |
| --- | --- | --- | --- | --- | --- |
| Embryonic rat cortical neurons | poly-D-lysine | Y | N | N | Y |
| hiPSC-derived cortical neurons | poly-L-ornithine + Laminin | Y | Y | Y | Y |
| hiPSC-derived hippocampal neurons | poly-L-ornithine + Laminin | N | N | Y | N |
| hiPSC-derived dopaminergic neurons | poly-L-ornithine + Laminin | Y | Y | N | Y |
| hiPSC-derived motor neurons | poly-L-ornithine + Matrigel ™ | Y | Y | Y | Y |

Example III

In the following experiment, aminated dendritic polyglycerol-based coatings were tested for their capacity to sustain neuronal cultures in vitro. These various coatings tested are: unmodified dendritic polyglycerol (dPGA), dPGA-linked to the cyclic form of the cell-binding peptide RGD (dPGA-RGD), dPGA-linked to the positively charged polypeptide poly-d-lysine (dPGA-PDL), dPGA-linked to the non-polar polypeptide poly-alanine (dPGA-pAla), dPGA-linked to the negatively charged polypeptide poly-glutamic acid (dPGA-pGlu), and uncoated glass. As can be seen in FIGS. 9A-9F, 7 DIV primary rat cortical neurons grown on these various dendritic polyglycerol coatings (linked to different peptide) were stained using the nuclear dye Hoechst to label living cells in culture.

Quantification of the number of cells in cultures as reported in FIG. 9G was carried out on the various cultures conducted with the various coatings as reported above.

The data in the FIGS. 9A-9G show that dPGA does not support cells in culture when they are linked to negatively charged polypeptide (poly-glutamic acid in this case "dPGA-pGlu"). The rationale is that the negatively charged polypeptide neutralizes the dendritic polyglycerol's positive charge which is important for the particle to adhere to culture surfaces and for the cells to adhere to the coating.

Linking the dendritic polyglycerol to a positively charged polypeptide that would increase the net positive charge of the coating (poly-d-lysine, see "dPGA-PDL") or to a neutral polypeptide that would not affect the aminated dendritic polyglycerol's charge (in this case cyclicRGD "dPGA-RGD" and poly-Alanine "dPGA-pAla") improves the capacity of the coating to maintain cells in vitro (more cells survived/adhered to the surface).

While the invention has been described in connection with specific embodiments thereof, it will be understood that the scope of the claims should not be limited by the preferred embodiments set forth in the examples, but should be given the broadest interpretation consistent with the description as a whole.

REFERENCES

Banker, G. A. 1980. 'Trophic interactions between astroglial cells and hippocampal neurons in culture', Science, 209: 809-10.

Brennand K J, et al. 'Modelling schizophrenia using human induced pluripotent stem cells' Nature. 2011; 473:221-225

Kriks, S., J. W. Shim, J. Piao, Y. M. Ganat, D. R. Wakeman, Z. Xie, L. Carrillo-Reid, G. Auyeung, C. Antonacci, A. Buch, L. Yang, M. F. Beal, D. J. Surmeier, J. H. Kordower, V. Tabar, and L. Studer. 2011. 'Dopamine neurons derived from human ES cells efficiently engraft in animal models of Parkinson's disease', Nature, 480: 547-51.

What is claimed is:

1. A cell or tissue culture system comprising (i) a solid support for the culture of adherent cells or adherent tissues and (ii) a plurality of cationic polyglycerol dendrimers associated to the surface of the solid support via electrostatic interactions, wherein each of the cationic polyglycerol dendrimer includes one or more functional amine group and is protonated at physiological pH.

2. The cell or tissue culture system of claim 1, wherein at least 25% of the functional groups of the plurality of the cationic polyglycerol dendrimer are functional amine groups.

3. The cell or tissue culture system of claim 1, wherein the plurality of the cationic polyglycerol dendrimers form aggregates on the surface of the solid support.

4. The cell or tissue culture system of claim 1, wherein the plurality of the cationic polyglycerol dendrimers are adhered to the surface of the solid support.

5. The cell or tissue culture system of claim 1, wherein the surface of the solid support is substantially planar.

6. The cell or tissue culture system of claim 1, wherein the solid support comprises glass, plastic or is a combination thereof.

7. The cell or tissue culture system of claim 6, wherein the plastic comprises polystyrene.

8. The cell or tissue culture system of claim 1 further comprising synthetic polypeptides associated to the surface of the solid support and/or to at least one of the plurality of the cationic polyglycerol dendrimer.

9. The cell or tissue culture system of claim 8, wherein the synthetic polypeptides comprise poly-L-lysine, poly-D-lysine and/or poly-alanine.

10. The cell or tissue culture system of claim 1 further comprising extracellular matrix components, or peptidic fragments thereof, associated to the surface of the solid support and/or to at least one of the plurality of the cationic polyglycerol dendrimer.

11. The cell or tissue culture system of claim 10, wherein the extracellular matrix components comprise collagen, elastin, fibronectin, laminin, thrombospondin, vitronectin or combinations thereof.

12. The cell or tissue culture system of claim 1 further comprising adherent cells.

13. The cell or tissue culture system of claim 12, wherein the adherent cells comprises motor neurons, cortical neurons, dopaminergic neurons and/or hippocampal neurons.

14. The cell or tissue culture system of claim 12, wherein the adherent cells lack the ability to grow on the surface of the solid support in the absence of the plurality of the cationic polyglycerol dendrimers associated to the surface of the solid support.

* * * * *